US010583011B2

(12) United States Patent
Lieberman et al.

(10) Patent No.: US 10,583,011 B2
(45) Date of Patent: *Mar. 10, 2020

(54) METHOD AND SYSTEM INCLUDING SLEEVES AND BROACHES FOR SURGICALLY PREPARING THE PATIENT'S BONE

(71) Applicant: DEPUY IRELAND UNLIMITED COMPANY, Co Cork (IE)

(72) Inventors: Jay R. Lieberman, Avon, CT (US); Benjamin J. Sordelet, Columbia City, IN (US); Richard Spencer Jones, Shropshire (GB); Timothy G. Vendrely, Fort Wayne, IN (US); Stephanie M. Wainscott, Warsaw, IN (US); Rebecca L. Chaney, Warsaw, IN (US); Joseph G. Wyss, Warsaw, IN (US); Stephen A. Hazebrouck, Winona Lake, IN (US); Aaron J. Matyas, Fort Wayne, IN (US)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 342 days.

This patent is subject to a terminal disclaimer.

(21) Appl. No.: 15/662,781

(22) Filed: Jul. 28, 2017

(65) Prior Publication Data

US 2017/0325964 A1 Nov. 16, 2017

Related U.S. Application Data

(60) Continuation of application No. 15/139,143, filed on Apr. 26, 2016, which is a division of application No. (Continued)

(51) Int. Cl.
*A61F 2/38* (2006.01)
*A61F 2/30* (2006.01)
(Continued)

(52) U.S. Cl.
CPC ........ *A61F 2/3859* (2013.01); *A61B 17/1659* (2013.01); *A61B 17/1675* (2013.01);
(Continued)

(58) Field of Classification Search
CPC ......................... A61B 17/1675; A61F 2/3859
See application file for complete search history.

(56) References Cited

U.S. PATENT DOCUMENTS

| 534,434 A | 2/1895 | Frost |
|---|---|---|
| 1,942,640 A | 1/1934 | Fromme |

(Continued)

FOREIGN PATENT DOCUMENTS

| CN | 2469899 Y | 1/2002 |
|---|---|---|
| CN | 101172062 A | 5/2008 |

(Continued)

OTHER PUBLICATIONS

English translation of Japanese Notification of Reason for Refusal issued in connection with Japanese Application No. 2013-195219, dated May 25, 2017, 5 pages.

(Continued)

*Primary Examiner* — Zade Coley
(74) *Attorney, Agent, or Firm* — Barnes & Thornburg LLP

(57) ABSTRACT

An orthopaedic surgical instrument system includes a first broach including a first end configured to be separately secured to a handle and a tapered body having a plurality of cutting teeth defined therein, and a second broach including a first end configured to be separately secured to the handle in place of the first broach, a first tapered body extending distally from a second end positioned opposite the first end, and a second tapered body extending distally from the first tapered body. The tapered body of the first broach and the first tapered body of the second broach have a first outer
(Continued)

geometry and the second tapered body has a second outer geometry different from the first outer geometry.

15 Claims, 15 Drawing Sheets

Related U.S. Application Data

13/832,490, filed on Mar. 15, 2013, now Pat. No. 9,320,603.

(60) Provisional application No. 61/703,404, filed on Sep. 20, 2012.

(51) Int. Cl.
  *A61B 17/16* (2006.01)
  *A61B 17/00* (2006.01)

(52) U.S. Cl.
  CPC .......... *A61F 2/30734* (2013.01); *A61F 2/389* (2013.01); *A61B 2017/00464* (2013.01); *A61F 2002/30233* (2013.01); *A61F 2002/30332* (2013.01); *A61F 2002/30433* (2013.01); *A61F 2002/30484* (2013.01); *A61F 2002/30616* (2013.01); *A61F 2002/30736* (2013.01); *A61F 2002/30738* (2013.01); *A61F 2250/006* (2013.01)

(56) References Cited

U.S. PATENT DOCUMENTS

| | | | |
|---|---|---|---|
| 2,379,796 | A | 7/1945 | Freeman et al. |
| 3,605,123 | A | 4/1969 | Hahn |
| 3,848,272 | A | 11/1974 | Noiles |
| 3,855,638 | A | 12/1974 | Pilliar |
| 4,219,893 | A | 9/1980 | Noiles |
| 4,301,553 | A | 11/1981 | Noiles |
| 4,536,894 | A | 8/1985 | Galante et al. |
| 4,549,319 | A * | 10/1985 | Meyer ............ A61F 2/30734 606/100 |
| 4,634,444 | A | 1/1987 | Noiles |
| 4,695,283 | A | 9/1987 | Aldinger |
| 4,716,894 | A | 1/1988 | Lazzeri et al. |
| 4,790,852 | A | 12/1988 | Noiles |
| 4,822,366 | A | 4/1989 | Bolesky |
| 4,846,839 | A | 7/1989 | Noiles |
| 4,854,496 | A | 8/1989 | Bugle |
| 5,061,270 | A | 10/1991 | Aboczky et al. |
| 5,061,271 | A | 10/1991 | Van Zile |
| 5,080,685 | A | 1/1992 | Bolesky et al. |
| 5,133,760 | A | 7/1992 | Petersen et al. |
| 5,152,792 | A | 10/1992 | Watkins et al. |
| D331,461 | S | 12/1992 | Lester |
| 5,181,928 | A | 1/1993 | Bolesky et al. |
| 5,182,921 | A | 2/1993 | Yan |
| 5,194,066 | A | 3/1993 | Van Zile |
| 5,226,915 | A | 7/1993 | Bertin |
| 5,250,051 | A | 10/1993 | Maryan |
| 5,284,483 | A | 2/1994 | Johnson |
| 5,286,260 | A | 2/1994 | Bolesky et al. |
| 5,290,313 | A | 3/1994 | Heldreth |
| 5,320,625 | A | 6/1994 | Bertin et al. |
| 5,330,534 | A | 7/1994 | Herrington et al. |
| 5,364,403 | A | 11/1994 | Petersen et al. |
| 5,370,706 | A | 12/1994 | Bolesky et al. |
| 5,441,501 | A * | 8/1995 | Kenyon ............ A61B 17/1659 606/85 |
| 5,457,857 | A | 10/1995 | Lam |
| 5,531,793 | A | 7/1996 | Kelman et al. |
| 5,540,697 | A | 7/1996 | Rehmann et al. |
| 5,556,433 | A | 9/1996 | Gabriel et al. |
| 5,584,837 | A | 12/1996 | Petersen |
| 5,593,449 | A | 1/1997 | Roberson, Jr. |
| 5,653,765 | A | 8/1997 | McTighe et al. |
| 5,658,294 | A | 8/1997 | Sederholm et al. |
| 5,658,349 | A | 8/1997 | Brooks et al. |
| 5,674,223 | A * | 10/1997 | Cipolletti ............ A61B 17/155 606/85 |
| 5,683,399 | A | 11/1997 | Jones et al. |
| 5,683,472 | A | 11/1997 | O'Neil et al. |
| 5,741,264 | A * | 4/1998 | Cipolletti ............ A61B 17/155 606/85 |
| 5,782,920 | A | 7/1998 | Colleran |
| 5,782,921 | A * | 7/1998 | Colleran ............ A61F 2/3859 623/20.15 |
| 5,824,097 | A * | 10/1998 | Gabriel ................ A61F 2/3859 623/23.15 |
| 5,876,459 | A | 3/1999 | Powell |
| 5,879,341 | A | 3/1999 | Odorzynski et al. |
| 5,879,391 | A | 3/1999 | Slamin |
| 5,906,644 | A | 5/1999 | Powell |
| 5,944,756 | A | 8/1999 | Fischetti et al. |
| 5,951,603 | A | 9/1999 | O'Neil et al. |
| 5,984,969 | A | 11/1999 | Matthews |
| 6,005,018 | A | 12/1999 | Cicierega et al. |
| 6,053,945 | A | 4/2000 | O'Neil et al. |
| 6,071,311 | A * | 6/2000 | O'Neil ............ A61F 2/30734 623/20.15 |
| 6,126,693 | A | 10/2000 | O'Neil et al. |
| 6,149,687 | A | 11/2000 | Gray, Jr. et al. |
| 6,171,342 | B1 * | 1/2001 | O'Neil ............ A61F 2/38 623/20.15 |
| 6,214,052 | B1 | 4/2001 | Burkinshaw |
| 6,264,699 | B1 | 7/2001 | Noiles et al. |
| 6,322,564 | B1 * | 11/2001 | Surma ............ A61B 17/1668 606/79 |
| 6,395,005 | B1 | 5/2002 | Lovell |
| 6,428,578 | B2 | 8/2002 | White |
| 6,443,991 | B1 | 9/2002 | Running |
| 6,447,549 | B1 | 9/2002 | Taft |
| 6,527,807 | B1 | 3/2003 | O'Neil et al. |
| 6,561,603 | B2 | 5/2003 | Knab et al. |
| 6,613,092 | B1 | 9/2003 | Kana et al. |
| 6,723,129 | B2 * | 4/2004 | Dwyer ............ A61F 2/30734 623/22.42 |
| 6,727,723 | B2 | 4/2004 | Shimizu et al. |
| 6,743,235 | B2 | 6/2004 | Subba Rao |
| 6,824,566 | B2 | 11/2004 | Kana et al. |
| 6,875,239 | B2 | 4/2005 | Gerbec et al. |
| 6,902,583 | B2 | 6/2005 | Gerbec et al. |
| 6,953,479 | B2 | 10/2005 | Carson et al. |
| 7,037,310 | B2 | 5/2006 | Murphy |
| 7,291,174 | B2 | 11/2007 | German et al. |
| 7,628,818 | B2 | 12/2009 | Hazebrouck et al. |
| 7,799,085 | B2 * | 9/2010 | Goodfried ............ A61F 2/30734 623/20.15 |
| 7,976,545 | B2 | 7/2011 | Hershberger |
| 8,128,703 | B2 | 3/2012 | Hazebrouck et al. |
| 8,382,849 | B2 | 2/2013 | Thomas |
| 8,424,183 | B2 | 4/2013 | Thomas |
| 8,562,616 | B2 | 10/2013 | May et al. |
| 8,764,758 | B2 | 7/2014 | Echeverri |
| 9,095,448 | B2 | 8/2015 | Birkbeck et al. |
| 9,320,603 | B2 | 4/2016 | Lieberman et al. |
| 2002/0125756 | A1 | 9/2002 | Asano |
| 2002/0133234 | A1 | 9/2002 | Sotereanos |
| 2003/0014120 | A1 | 1/2003 | Carson et al. |
| 2003/0204267 | A1 | 10/2003 | Hazebrouck et al. |
| 2003/0204268 | A1 | 10/2003 | Gerbec et al. |
| 2004/0049285 | A1 * | 3/2004 | Haas ............ A61F 2/30734 623/20.15 |
| 2004/0073225 | A1 | 4/2004 | Subba Rao |
| 2004/0152972 | A1 | 8/2004 | Hunter |
| 2004/0172139 | A1 | 9/2004 | Dwyer et al. |
| 2005/0075736 | A1 | 4/2005 | Collazo |
| 2005/0107799 | A1 | 5/2005 | Graf et al. |
| 2005/0107883 | A1 * | 5/2005 | Goodfried ............ A61F 2/30734 623/20.15 |
| 2005/0149052 | A1 | 7/2005 | Meek |
| 2005/0149054 | A1 | 7/2005 | Gorek |
| 2005/0154470 | A1 | 7/2005 | Sekel |

(56) References Cited

U.S. PATENT DOCUMENTS

| | | | |
|---|---|---|---|
| 2005/0234462 A1 | 10/2005 | Hershberger | |
| 2005/0288676 A1* | 12/2005 | Schnieders | A61B 17/1659 606/79 |
| 2006/0030945 A1* | 2/2006 | Wright | A61F 2/30721 623/20.15 |
| 2006/0142867 A1 | 6/2006 | Metzger et al. | |
| 2006/0167554 A1* | 7/2006 | Heck | A61F 2/28 623/20.15 |
| 2006/0184177 A1 | 8/2006 | Echeverri | |
| 2007/0225821 A1 | 9/2007 | Reubelt | |
| 2008/0234830 A1 | 9/2008 | Hershberger et al. | |
| 2009/0088862 A1 | 4/2009 | Thomas et al. | |
| 2009/0105768 A1 | 4/2009 | Cragg et al. | |
| 2010/0076565 A1* | 3/2010 | Thomas | A61F 2/30734 623/20.16 |
| 2010/0076566 A1 | 3/2010 | Serafin, Jr. et al. | |
| 2010/0114323 A1* | 5/2010 | Deruntz | A61B 17/1675 623/20.21 |
| 2010/0137871 A1 | 6/2010 | Borja | |
| 2010/0249657 A1 | 9/2010 | Nycz et al. | |
| 2011/0027100 A1 | 2/2011 | Cummane et al. | |
| 2011/0184419 A1 | 7/2011 | Meridew et al. | |
| 2011/0276053 A1 | 11/2011 | Birkebeck et al. | |
| 2012/0016482 A1 | 1/2012 | Mooradian | |
| 2012/0330319 A1 | 12/2012 | Birkbeck et al. | |
| 2013/0085577 A1 | 4/2013 | Link et al. | |
| 2013/0325136 A1* | 12/2013 | Thomas | A61B 17/157 623/20.32 |
| 2014/0081408 A1 | 3/2014 | Lieberman et al. | |
| 2014/0081409 A1 | 3/2014 | James et al. | |
| 2014/0081410 A1 | 3/2014 | Lieberman et al. | |
| 2014/0081411 A1 | 3/2014 | Lieberman et al. | |
| 2014/0378984 A1 | 12/2014 | Birkbeck et al. | |

FOREIGN PATENT DOCUMENTS

| | | |
|---|---|---|
| CN | 202168871 U | 3/2012 |
| DE | 10202582 C1 | 9/2003 |
| EP | 0457222 A1 | 5/1991 |
| EP | 0947181 A2 | 3/1999 |
| EP | 1623686 A2 | 2/2006 |
| EP | 1920713 A2 | 5/2008 |
| FR | 2733411 A1 | 4/1995 |
| FR | 2729560 A1 | 7/1996 |
| JP | 2010115487 A | 5/2010 |
| JP | 2012-165889 A | 9/2012 |
| WO | 91/18563 A1 | 12/1991 |
| WO | 9730661 A1 | 8/1997 |
| WO | 2001030247 A1 | 5/2001 |
| WO | 2003057087 A2 | 7/2003 |
| WO | 2003065939 A1 | 8/2003 |
| WO | 2004030556 A2 | 4/2004 |
| WO | 2005046475 A1 | 5/2005 |
| WO | 2006099270 A2 | 9/2006 |
| WO | 2007053905 A1 | 5/2007 |
| WO | 2010128320 A1 | 11/2010 |
| WO | 2010145769 A1 | 12/2010 |
| WO | 2011095804 A1 | 8/2011 |

OTHER PUBLICATIONS

European Search Report, European Application No. 13185435.8-1654, dated Dec. 11, 2013, 7 pages.
European Search Report, European Application No. 13185436.6-1654, dated Dec. 12, 2013, 8 pages.
Partial European Search Report, European Application No. 13185432.5-1654, dated Jan. 2, 2014, 7 pages.
EPO Search Report From Corresponding EPO Patent App. 13185424.2-1654, dated Nov. 5, 2013, 6 Pages.
European Partial Search Report, European Application No. 14194276.3-1654, dated Jun. 12, 2015, 7 pages.
European Extended Search Report, European Application No. 13185432.5-1654, dated Feb. 19, 2014, 13 pages.
Biomet, "Orthopaedic Salvage System Overview", Aug. 15, 2005, 153 pages.
Depuy Reconstructive/Revision Products, 0608-46-000, 2000 (pp. 182-184).
Depuy Orthopaedics, Inc., PFC SIGMA Knee System With Rotating Platform Technical Monograph, 3M0800, 0611-29-050, 1999, Depuy Orthopaedics, Inc.
Depuy Orthopaedics, Inc., LCS Complete Mobile-Bearing Knee System, 2001, Depuy Prthopaedics, Inc.
S-ROM Noiles Rotating Hinge Surgical Technique & Reference Guide, 0601-98-050 (Rev. 2), Depuy Orthopaedics, Inc., 2002, 44 Pages.
Extended European Search Report dated Oct. 19, 2015 and issued in connection with European Patent Application No. 14194276.3-1654, 10 pages.
Depuy International Ltd., Pinnacle Acetabular Cup System Surgical Technique; Cat. No. 9068-80-050, 2003, 40 pages.
Depuy International Ltd., Pinnacle Acetabular Cur System Surgical Technique; Cat. No. 9068-80-050 version 2; June R009, 36 pages.
DePuy International Ltd. Pinnacle Acetabular Cup System Surgical Technique; Cat. No. 0611-42-050 (Rev. 3); Aug. 24, 2004, 49 pages.
Langston, et al., "The Effect of Component Size and Orientation on the Concentrations of Metal Ions After Resurfacing Arthroplasty of the Hip," The Journal of Bone & Joint Surgery, pp. 1143-1152, vol. 90-8, No. 9, Sep. 2008.
Murray, D.W., "The Definition and Measurement of Acetabular Orientation," The Journal of Bone & Joint Surgery, pp. 228-232, vol. 75-8, No. 2, Mar. 1993.
European Search Report for European Application No. 13161262.4-1654, dated Jun. 20, 2013, 8 pages.
L. Fabeck, et al., "A Method to Measure Acetabular Cup Anteversion After Total Hip Replacement," Acta Orthopaedica Belgica. vol. 65-4—1999, 485-491.
Search Report issued by the State Intellectual Property Office of People's Republic China in connection with Chinese Application N. 201310435609.7, dated Jul. 8, 2016, 2 pages.
Search Report issued by the State Intellectual Property Office of the People's Republic China in connection with Chinese Application No. 201310459343.X, undated, 3 pages.
Search Report issued by the State Intellectual Property Office of the People's Republic China in connection with Chinese Application No. 201310435611.4, dated May 25, 2016, 2 pages.
English translation of Japanese Office Action, Japanese Application No. 2013-195222, dated May 9, 2017, 4 pages.

\* cited by examiner

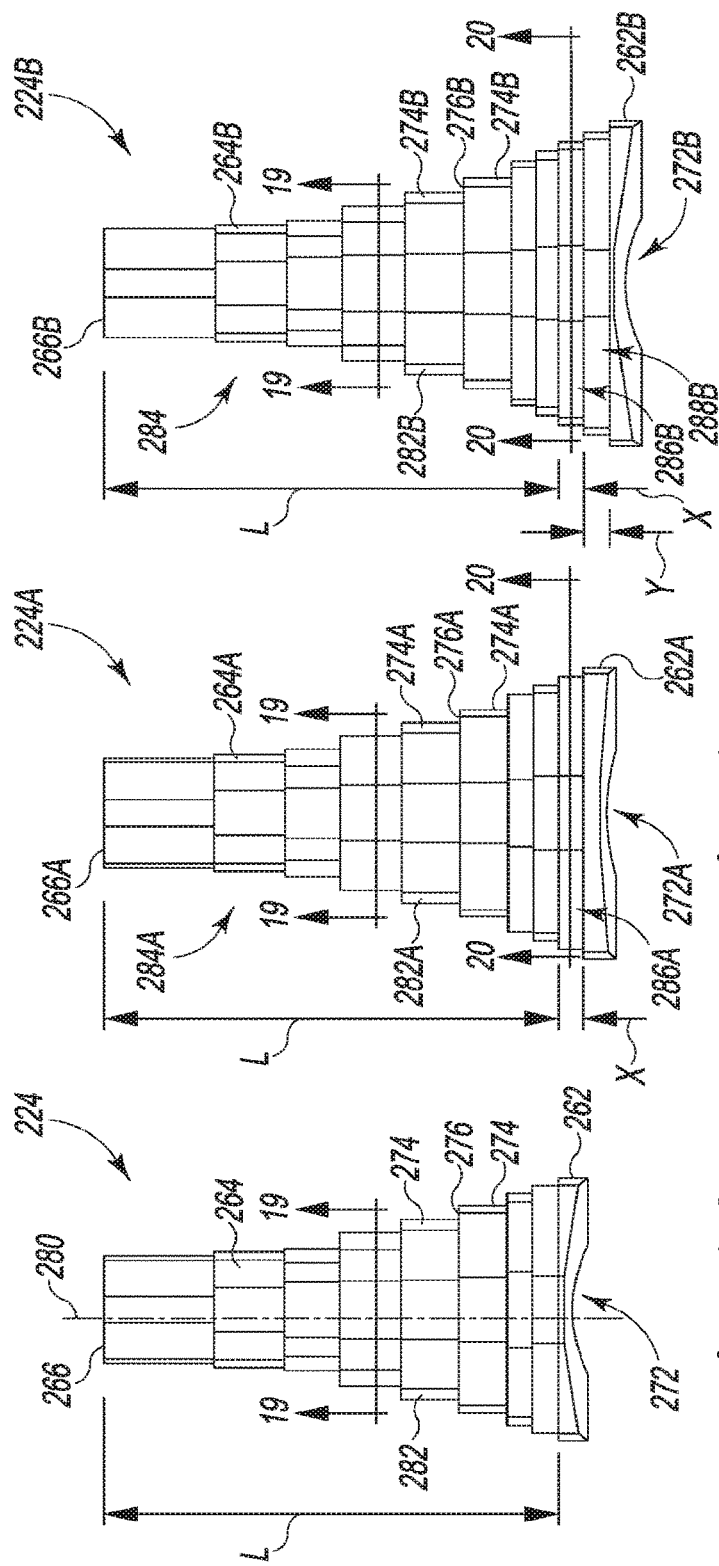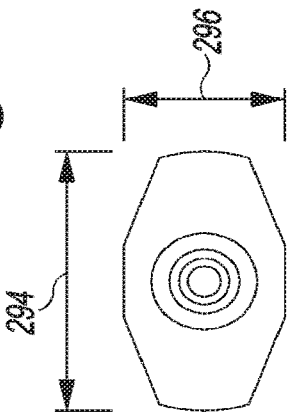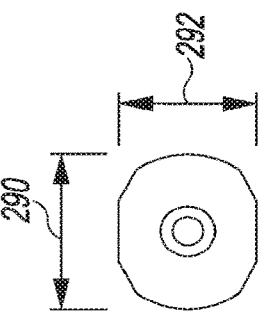

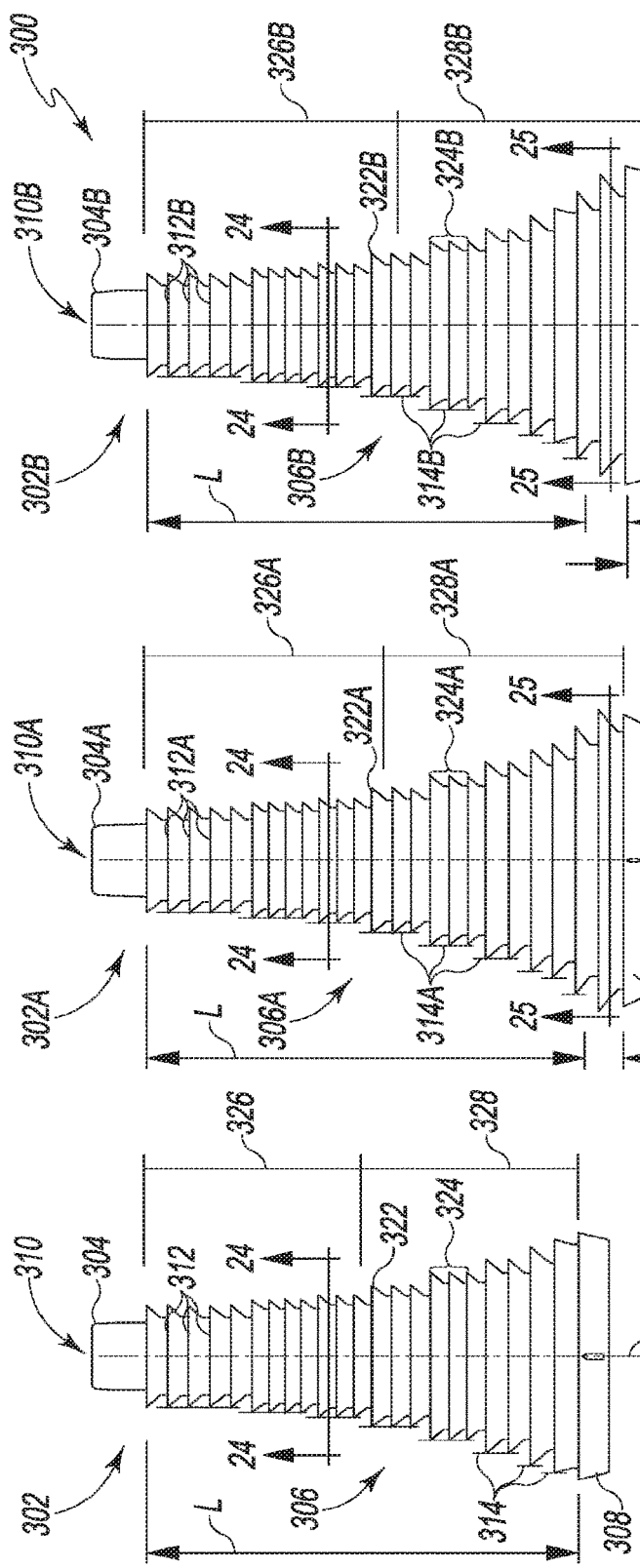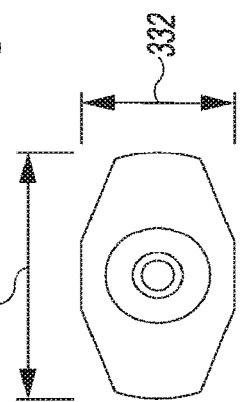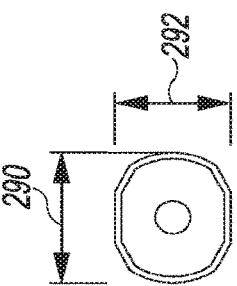

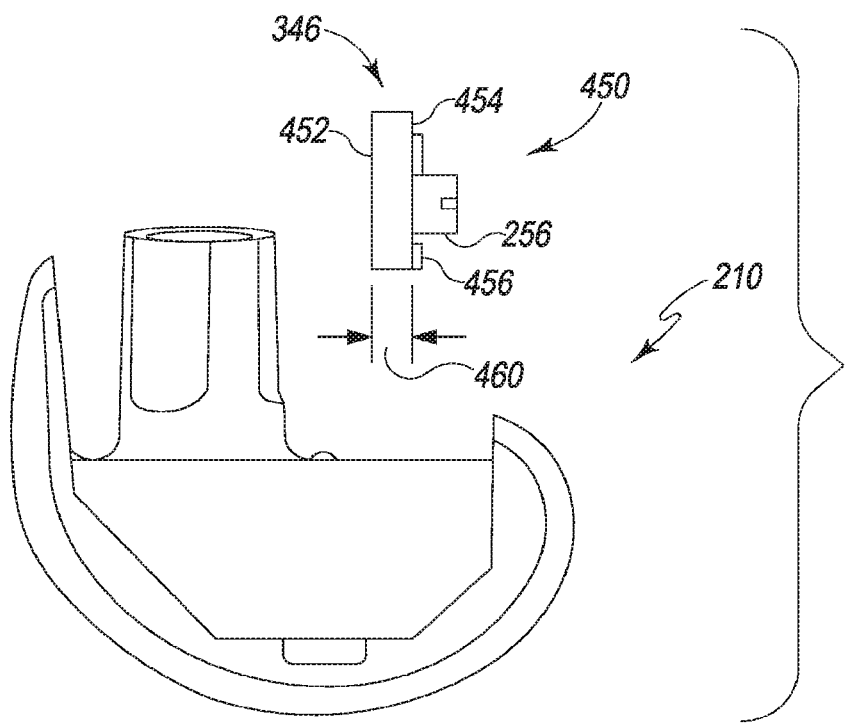
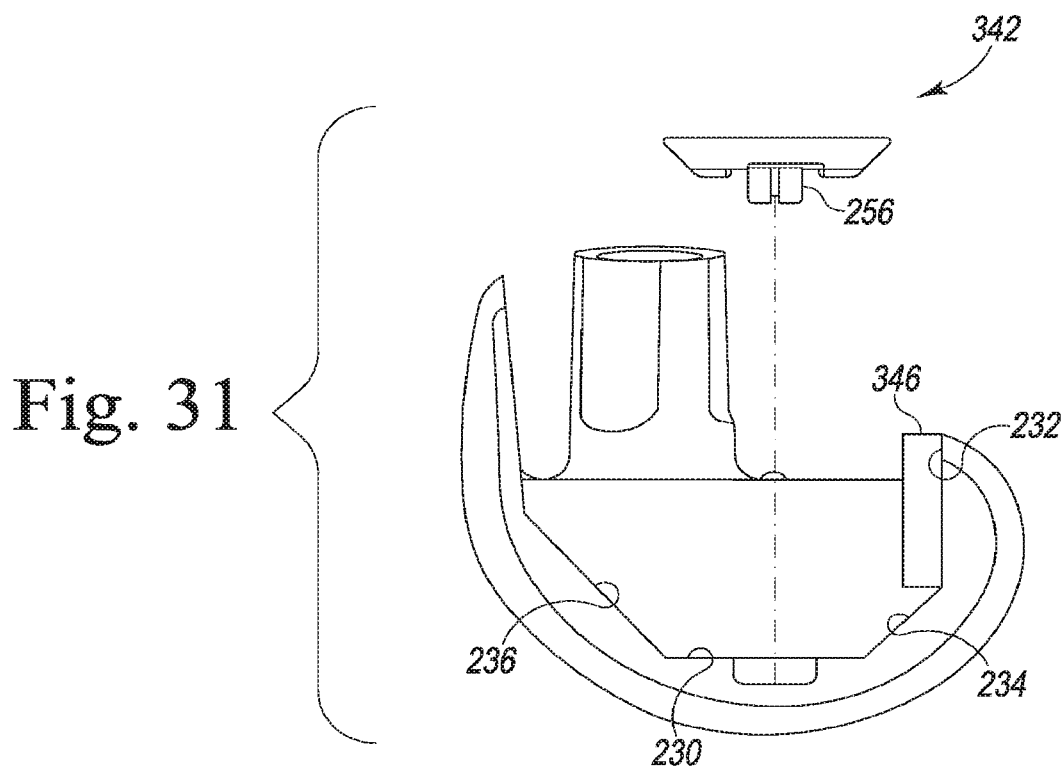

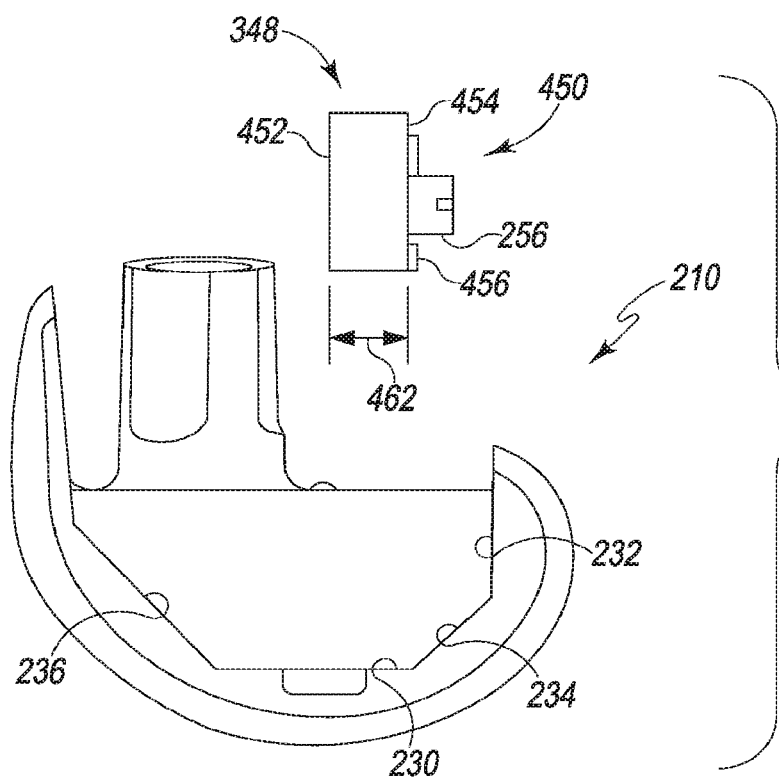
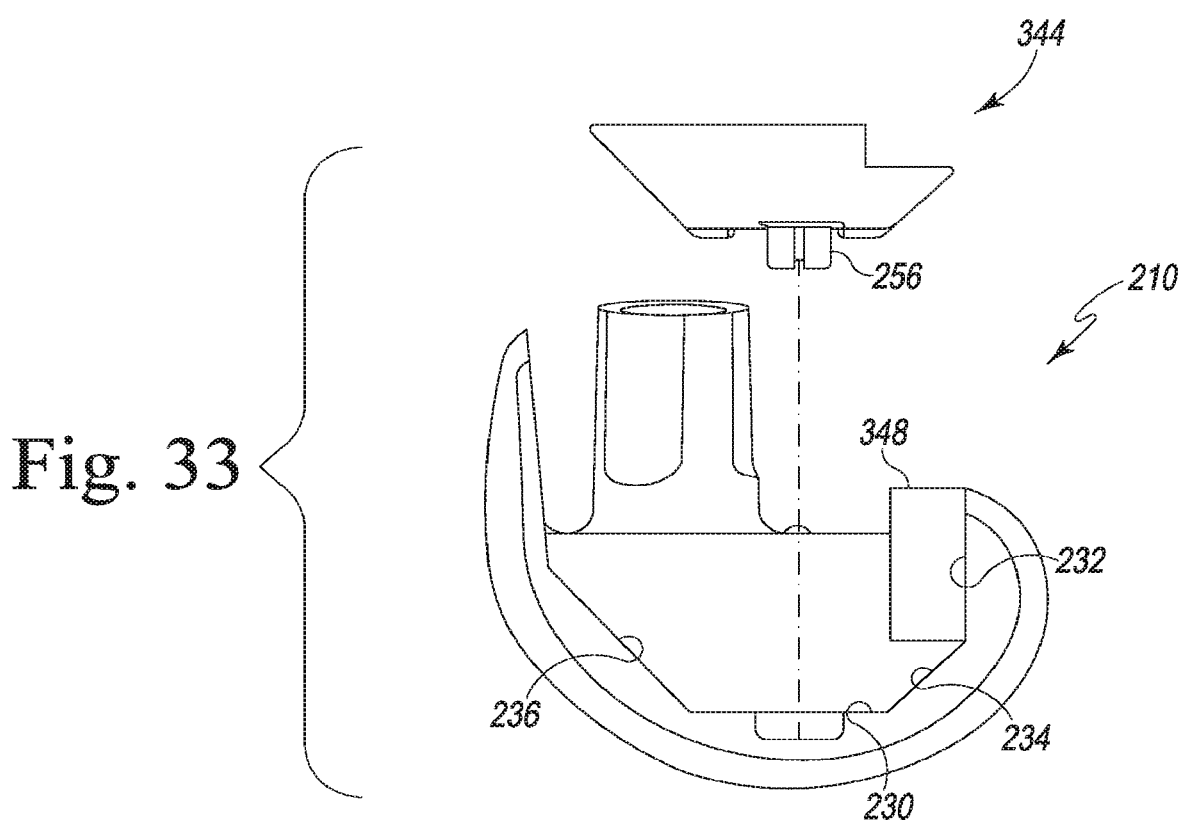

METHOD AND SYSTEM INCLUDING SLEEVES AND BROACHES FOR SURGICALLY PREPARING THE PATIENT'S BONE

This application claims priority to U.S. patent application Ser. No. 15/139,143, which claims priority to U.S. patent application Ser. No. 13/832,490, now U.S. Pat. No. 9,320,603, filed Mar. 15, 2013, which claimed priority under 35 U.S.C. § 119 to U.S. Prov. App. No. 61/703,404 filed Sep. 20, 2012, entitled "Modular Knee Prosthesis System with Multiple Lengths of Sleeves Sharing Common Geometry," the entirety of each of which is incorporated herein by reference in its entirety.

CROSS-REFERENCE

Cross reference is made to U.S. patent application Ser. No. 13/832,439 entitled "MODULAR KNEE PROSTHESIS SYSTEM WITH MULTIPLE LENGTHS OF SLEEVES SHARING A COMMON GEOMETRY," and U.S. patent application Ser. No. 13/832,415, now U.S. Pat. No. 9,532,879, entitled "FEMORAL KNEE PROSTHESIS SYSTEM WITH AUGMENTS AND MULTIPLE LENGTHS OF SLEEVES SHARING A COMMON GEOMETRY," each of which is assigned to the same assignee as the present application, each of which is filed concurrently herewith, and each of which is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a revision knee replacement procedure.

BACKGROUND

The knee joint basically consists of the bone interface of the distal end of the femur and the proximal end of the tibia. Appearing to cover or at least partially protect this interface is the patella, which is a sesamoid bone within the tendon of the long muscle (quadriceps) on the front of the thigh. This tendon inserts into the tibial tuberosity and the posterior surface of the patella is smooth and glides over the femur.

The femur is configured with two knob like processes (the medial condyle and the lateral condyle) which are substantially smooth and which articulate with the medial plateau and the lateral plateau of the tibia, respectively. The plateaus of the tibia are substantially smooth and slightly cupped thereby providing a slight receptacle for receipt of the femoral condyles.

When the knee joint is damaged whether as a result of an accident or illness, a prosthetic replacement of the damaged joint may be necessary to relieve pain and to restore normal use to the joint. Typically the entire knee joint is replaced by means of a surgical procedure that involves removal of the surfaces of the corresponding damaged bones and replacement of these surfaces with prosthetic implants. This replacement of a native joint with a prosthetic joint is referred to as a primary total-knee arthroplasty.

On occasion, the primary knee prostheses fails. Failure can result from many causes, including wear, aseptic loosening, osteolysis, ligamentous instability, arthrofibrosis and patellofemoral complications. When the failure is debilitating, revision knee surgery may be necessary. In a revision, the primary knee prosthesis is removed and replaced with components of a revision prosthetic knee system.

Knee implant systems for both primary and revision applications are available from a variety of manufacturers, including DePuy Orthopaedics, Inc. of Warsaw, Ind. DePuy and others offer several different systems for both primary and revision applications. For example, DePuy Orthopaedics offers the P.F.C. SIGMA® Knee System, the LCS® Total Knee System, and the S-ROM Modular Total Knee System. These orthopaedic knee systems includes several components, some appropriate for use in primary knee arthroplasty and some appropriate for use in revision surgery.

DePuy Orthopaedics also offers other orthopaedic implant systems for other applications. One such system is the LPS System. The LPS System is provided for use in cases of severe trauma and disease. In such cases, the trauma or disease can lead to significant amounts of bone loss. The LPS System provides components that can replace all or significant portions of a particular bone, such as the femur. The DePuy LPS System is described more fully in U.S. patent application Ser. No. 10/135,791, entitled "Modular Limb Preservation System", filed Apr. 30, 2002 by Hazebrouck et al. (U.S. Pat. Pub. No. 2003-0204267), which is incorporated by reference herein in its entirety.

In some patients, the metaphysis of the bone near the joint presents cavitary defects that are not completely filled by standard knee implants. The presence of such metaphyseal defects can result in loosening of the prosthetic implant over time, compromising the stability of the prosthetic implant and frequently requiring revision of the prosthetic implant.

To fill metaphyseal cavitary defects, knee systems with modular metaphyseal sleeves have been provided. Such sleeves are illustrated, for example, in: U.S. Pat. Pub. No. 2010/0114323, entitled "Knee Prosthesis Kit with Winged Sleeves and Milling Guide;" U.S. Pat. Pub. No. 2006/0030945A1, entitled "Modular Orthopaedic Implant System With Multi-Use Stems;" U.S. Pat. No. 7,799,085, entitled "Modular Implant System With Fully Porous Coated Sleeve;" U.S. Pat. No. 7,291,174, entitled "Prosthetic Tibial Component With Modular Sleeve;" U.S. Pat. No. 6,171,342, entitled "Medical Fastening System;" U.S. Pat. No. 5,824,097, entitled "Medical Fastening System;" U.S. Pat. No. 5,782,921, entitled "Modular Knee Prosthesis;" and U.S. Pat. No. 4,634,444, entitled "Semi-Constrained Artificial Joint." Such sleeves have been used in commercially available prosthetic knee implant systems, such as the P.F.C. SIGMA.® Knee System, the LCS® Total Knee System, the S-ROM Modular Total Knee System and the LPS System, all available from DePuy Orthopaedics, Inc. of Warsaw, Ind.

Modular sleeves have also been used in hip implant systems, as illustrated, for example, in: U.S. Pat. No. 6,264,699, entitled "Modular Stem and Sleeve Prosthesis;" and U.S. Pat. No. 4,790,852, entitled "Sleeves for Affixing Artificial Joints to Bone." Such hip sleeves have been used in commercially available prosthetic hip implant systems, such as the S-ROM hip systems, available from DePuy Orthopaedics, Inc. of Warsaw, Ind.

The disclosures of all of the above patent applications and patents are incorporated by reference herein in their entireties.

In knee systems with modular metaphyseal sleeves, the conventional shape of many of the sleeves is generally an elliptical cone with a large ellipse profile close to the joint line tapering down to a smaller elliptical or circular profile at the termination of the component distal to the joint line.

Generally, the sleeves have a terraced or stepped outer surface and an inner channel for frictional fixation to another component. This geometry fills cavitary defects in the metaphysis, allows for a wider surface area for load transfer through the joint and provides rotational stability for the articulating components of the prosthesis.

The outer surface of the sleeve is supported by solid bony structure or the bone bed. In the case of the distal femur, patient anatomy and the condition of the bone, particularly in a revision surgery, may require that the distal femur be resected to a more proximal level. Implanting a prosthetic distal femoral component and sleeve at this more proximal level may elevate the joint line (that is, the line defined by the articulation of the articular surfaces of the distal femoral component and proximal tibial component). Elevation of the joint line may adversely affect performance of the prosthetic knee system: the positions of the collateral ligament attachments to the femur relative to the joint line may impact knee kinematics, the articulation of the patella against the femoral component will be impacted, and the function of the extensor mechanism will also be impacted.

Prosthetic knee implant systems have commonly included femoral augments for use on the distal and posterior bone-facing surfaces of the femoral implant components. Examples of such augments are disclosed in U.S. Pat. Nos. 6,005,018 and 5,984,969, which are incorporated by reference herein in their entireties. Such components serve to augment the inferior and posterior portions of the femoral component to add additional thickness to compensate for the lack of sufficient boney tissue, allowing the joint line to be distalized. However, with the femoral component so distalized, the metaphyseal sleeve used with the femoral component may no longer be optimally seated on a healthy bone bed. To compensate, surgeons may sometimes opt to use a larger size of metaphyseal sleeve. Because of differences in the geometries of differently-sized metaphyseal sleeves, changing to a larger size requires that the surgeon prepare the bone cavity a second time so that the cavity will accept the geometry of the larger size of metaphyseal sleeve.

Accordingly, a need exists for a knee prosthesis system that allows the surgeon the flexibility to optimize the position of the joint line while also allowing for a metaphyseal sleeve to be efficiently and optimally positioned on a healthy bone bed.

SUMMARY

A modular knee implant system that allows the surgeon to prepare the bone to receive a metaphyseal sleeve and to optimize the position of the joint line without further bone preparation to receive a different size of metaphyseal sleeve is provided.

According to one aspect of the present disclosure, a modular knee prosthesis system is provided. The system includes a distal femoral implant component, a proximal tibial implant component and two metaphyseal members. The distal femoral implant component has a pair of spaced, curved distal condylar surfaces and a stem. The stem has an outer surface tapering from a distal end in the proximal direction. The outer surface of the stem has a maximum outer diameter at the distal end and a smaller outer diameter at a second position proximal to the distal end. The proximal tibial implant component has an articulating surface to receive and articulate with the distal articulating surfaces of the distal femoral component and a stem. The tibial stem has an outer surface tapering from a proximal end in the distal direction. The outer surface of the tibial stem has a maximum outer diameter at the proximal end and a smaller outer diameter at a second position distal to the proximal end. The first metaphyseal member has an outer surface that tapers in a proximal direction and an inner surface defining a tapered bore sized and shaped to be mountable on the stem of one of the implant components and to create a frictional lock between the stem and the first metaphyseal member. The outer surface of the first metaphyseal member comprises a stepped portion having a plurality of steps. Each step has a maximum medial-lateral dimension and a maximum anterior-posterior dimension. The stepped portion of the first metaphyseal sleeve has an overall axial length L. The second metaphyseal member has an outer surface that tapers in a proximal direction and an inner surface defining a tapered bore sized and shaped to be mountable on the stem of one of the implant components and to create a frictional lock between the stem component and the second metaphyseal member. The outer surface of the second metaphyseal member comprises a stepped portion having a plurality of steps. Each step has a maximum medial-lateral dimension and a maximum anterior-posterior dimension. The stepped portion of the second metaphyseal sleeve has an overall axial length L+X and has a common geometry with the first metaphyseal sleeve over axial length L: over axial length L, the maximum medial-lateral dimension and maximum anterior-posterior dimension of each step is the same as the maximum medial-lateral dimension and maximum anterior-posterior dimension of each step over the axial length L of the stepped portion of the first metaphyseal member. With this common geometry over axial length L, the same prepared bone space will receive either the first metaphyseal member or the second metaphyseal member.

In an illustrative embodiment, the first metaphyseal member and the second metaphyseal member have the same number of steps over axial length L of the stepped portions of the first metaphyseal member and the second metaphyseal member.

In a more particular embodiment, each step of the stepped portion of the first metaphyseal member has an axial height, each step of the stepped portion of the second metaphyseal member has an axial height, and the axial heights of corresponding steps of the first metaphyseal member and the second metaphyseal member are the same.

In another illustrative embodiment, the system also includes a third metaphyseal member having an outer surface that tapers in a proximal direction and an inner surface defining a tapered bore sized and shaped to be mountable on the stem of one of the implants components and to create a frictional lock between the stem and the third metaphyseal member. The outer surface of the third metaphyseal member comprises a stepped portion having a plurality of steps. Each step has a maximum medial-lateral dimension and a maximum anterior-posterior dimension. The stepped portion having an overall axial length L+X+Y. The maximum medial-lateral dimension and maximum anterior-posterior dimension of each step over the axial length L of the stepped portion of the third metaphyseal member is the same as the maximum medial-lateral dimension and maximum anterior-posterior dimension of each step over the axial length L of the stepped portion of the first metaphyseal member and the second metaphyseal member. The maximum medial-lateral dimension and maximum anterior-posterior dimension of each step over the axial length L+X of the stepped portion of the third metaphyseal member is the same as the maximum medial-lateral dimension and maximum anterior-posterior dimension of each step over the axial length L+X of the stepped portion of the second metaphyseal member.

In another illustrative embodiment, the tapered bore of the first metaphyseal member is sized and shaped to be mountable on the stem of the distal femoral implant component and to create a frictional lock between the stem of the distal femoral implant component and the first metaphyseal member and the tapered bore of the second metaphyseal member is sized and shaped to be mountable on the stem of the distal femoral implant component and to create a frictional lock between the stem of the distal femoral implant component and the first metaphyseal member. In this embodiment, the contact between the articulating surfaces of the tibial member and the distal femoral component define a first joint line when the distal femoral component is assembled with the first metaphyseal member and the contact between the articulating surfaces of the tibial member and the distal femoral component define a second joint line when the distal femoral component is assembled with the second metaphyseal member. The second joint line is more distal than the first joint line in this embodiment.

In a more particular embodiment, the distance between the first joint line and the second joint line corresponds with the difference between the overall axial lengths of the first metaphyseal member and the second metaphyseal member and defines a distal offset.

According to another aspect of the present invention, a modular knee prosthesis system comprises a distal femoral component, a first metaphyseal member and a second metaphyseal member. The distal femoral component has a pair of spaced, curved distal condylar surfaces and a stem having an outer surface tapering from a distal end in the proximal direction. The outer surface of the femoral stem has a maximum outer diameter at the distal end and a smaller outer diameter at a second position proximal to the distal end. The first metaphyseal member includes an inner surface defining a tapered bore sized and shaped to be mountable on the stem of the distal femoral component and to create a frictional lock between the stem of the distal femoral component and the first metaphyseal member. The tapered bore extends proximally from an opening at the distal end of the first metaphyseal member. The first metaphyseal member also includes a tapered stepped outer surface having an axial length L. The second metaphyseal member includes an inner surface defining a tapered bore sized and shaped to be mountable on the stem of the distal femoral component and to create a frictional lock between the stem of the distal femoral component and the second metaphyseal member, the tapered bore extending proximally from an opening at the distal end of the second metaphyseal member. The second metaphyseal member includes a tapered stepped outer surface having an axial length L+X. The tapered stepped outer surface of the first metaphyseal member and the tapered stepped outer surface of the second metaphyseal member have the same shape and the same medial-lateral dimensions and the same anterior-posterior dimensions over axial length L. When the first metaphyseal member is mounted on the distal femoral component with the first metaphyseal member frictionally locked to the distal femoral component, the assembly has a maximum axial length. When the second metaphyseal member is mounted on the distal femoral component with the second metaphyseal member frictionally locked to the distal femoral component, the assembly has a maximum axial length. The maximum axial length of the assembly of the second metaphyseal member and the distal femoral component is greater than the maximum axial length of the assembly of the first metaphyseal member and the distal femoral component.

In an illustrative embodiment, the first metaphyseal member and the second metaphyseal member have the same number of steps over axial length L of the tapered stepped outer surface of the first metaphyseal member and the tapered stepped outer surface of the second metaphyseal member.

In a more particular embodiment, each step of the tapered stepped outer surface of the first metaphyseal member has an axial height and each step of the tapered stepped outer surface of the second metaphyseal member has an axial height. The axial heights of corresponding steps of the first metaphyseal member and the second metaphyseal member are the same.

In another illustrative embodiment, the system further comprises a third metaphyseal member including an inner surface defining a tapered bore sized and shaped to be mountable on the stem of the distal femoral component and to create a frictional lock between the stem of the distal femoral component and the first metaphyseal member. The tapered bore extends proximally from an opening at the distal end of the first metaphyseal member. The first metaphyseal member includes a tapered stepped outer surface having an axial length L+X+Y. When the third metaphyseal member is mounted on the distal femoral component with the third metaphyseal member frictionally locked to the distal femoral component, the assembly has a maximum axial length. The maximum axial length of the assembly of the third metaphyseal member and the distal femoral component is greater than the maximum axial length of the assembly of the second metaphyseal member and the distal femoral component.

In another illustrative embodiment, the distal femoral component has a distal bone-facing surface and the system further comprises a distal femoral augment. The distal femoral augment has a thickness that is substantially the same as X.

BRIEF DESCRIPTION OF THE DRAWINGS

The detailed description particularly refers to the following figures, in which:

FIG. 16 is a medial-lateral view of one size of metaphyseal sleeves of the modular knee prosthesis system of FIG. 15;

FIG. 17 is a medial-lateral view of another size of metaphyseal sleeves of the modular knee prosthesis system of FIG. 15;

FIG. 18 is a medial-lateral view of another size of metaphyseal sleeves of the modular knee prosthesis system of FIG. 15;

FIG. 19 is a cross sectional plan view taken along the lines 19-19 in FIGS. 16-18;

FIG. 20 is a cross sectional plan view taken along the lines 20-20 in FIGS. 17-18;

FIG. 21 is a medial-lateral view of a surgical broach of an orthopaedic surgical instrument system for use with the modular knee prosthesis system of FIG. 15;

FIG. 22 is a medial-lateral of another size of surgical broach of the orthopaedic surgical instrument system;

FIG. 23 is a medial-lateral of another size of surgical broach of the orthopaedic surgical instrument system;

FIG. 24 is a cross sectional plan view taken along the lines 24-24 in FIGS. 21-23;

FIG. 25 is a cross sectional plan view taken along the lines 25-25 in FIGS. 22-23;

FIG. 30 is an elevation view of the femoral component of FIG. 15 and a posterior augment;

FIG. 31 is a view similar to FIG. 30 showing the posterior augment secured to the femoral component and the distal augment of FIGS. 26-27;

FIG. 32 is an elevation view of the femoral component of FIG. 15 and another size of posterior augment;

FIG. 33 is a view similar to FIG. 32 showing the posterior augment secured to the femoral component and the distal augment of FIGS. 28-29;

DETAILED DESCRIPTION OF THE DRAWINGS

Figure 1:
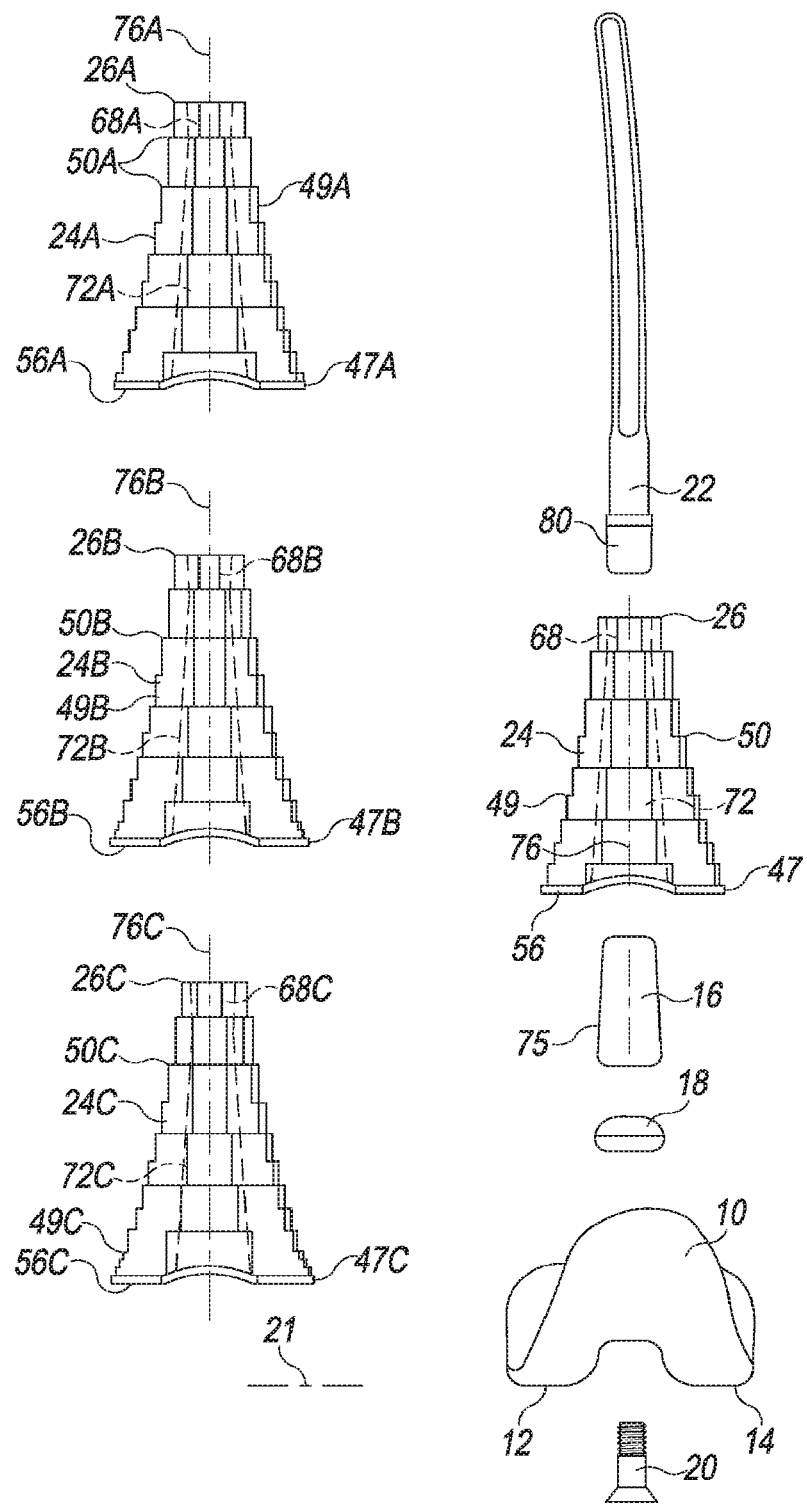
FIG. 1 is a view of the femoral components of a modular knee prosthesis system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

FIG. 1 illustrates an example of the femoral components of a modular knee prosthesis system illustrating the principles of the present invention. The femoral components of the system include a distal femoral component 10 with distal curved convex condylar surfaces 12, 14. The illustrated distal femoral component is a posterior stabilized component. The system illustrated in FIG. 1 also includes a femoral stem 16, along with a collar 18 for placement between the stem 16 and the distal femoral component 10 and a bolt 20 so that the stem 16 and collar 18 may be selectively mounted on the distal femoral component. Each stem 16 has a frusto-conical outer surface that is smooth and tapers from a maximum outer diameter at the distal end to smaller outer diameters at positions proximal to the distal end. Stem extensions 22 are also provided. All of the above components may be standard parts of the P.F.C. SIGMA.® Knee System available from DePuy Orthopaedics, Inc. of Warsaw, Ind., for example. Each stem 16 in the illustrated embodiments is an adapter with features like those illustrated in U.S. Pat. Pub. No. 2006/0030945, entitled "Modular Orthopaedic Implant System with Multi-Use Stems." The stems 16 may also have features like those illustrated in U.S. Pat. No. 6,171,342, entitled "Medical Fastening System," U.S. Pat. No. 5,824,097, entitled "Medical Fastening System," U.S. Pat. No. 5,782,921, entitled "Modular Knee Prosthesis." Also as described in U.S. Pat. Pub. No. 2006/0030945, the stem extension may have features other than those illustrated in FIG. 1. It should be understood that these components are described for purposes of illustration only; the present invention is not limited to any particular type of distal femoral component or stem or any other particular component unless expressly called out in the claims. For example, in some embodiments, the femoral component 10 may have an integral stem 16 instead of the illustrated stem adapter 16, collar 18 and bolt 20.

In the embodiment of FIG. 1, the femoral components of the illustrated system include a plurality of sizes of metaphyseal sleeves 24, 24A, 24B, 24C. As described in more detail below, the geometries of the exterior surfaces of the four sizes of metaphyseal sleeves 24, 24A, 24B, 24C are the same over a substantial portion of their axial lengths. It should be understood that multiple sizes of distal femoral components 10 and stem extensions 22 would typically be included in the modular knee prosthesis system. It should also be understood that a modular knee prosthesis system utilizing the principles of the present invention may include fewer or more sizes of metaphyseal sleeves 24, 24A, 24B, 24C.

Figure 2:
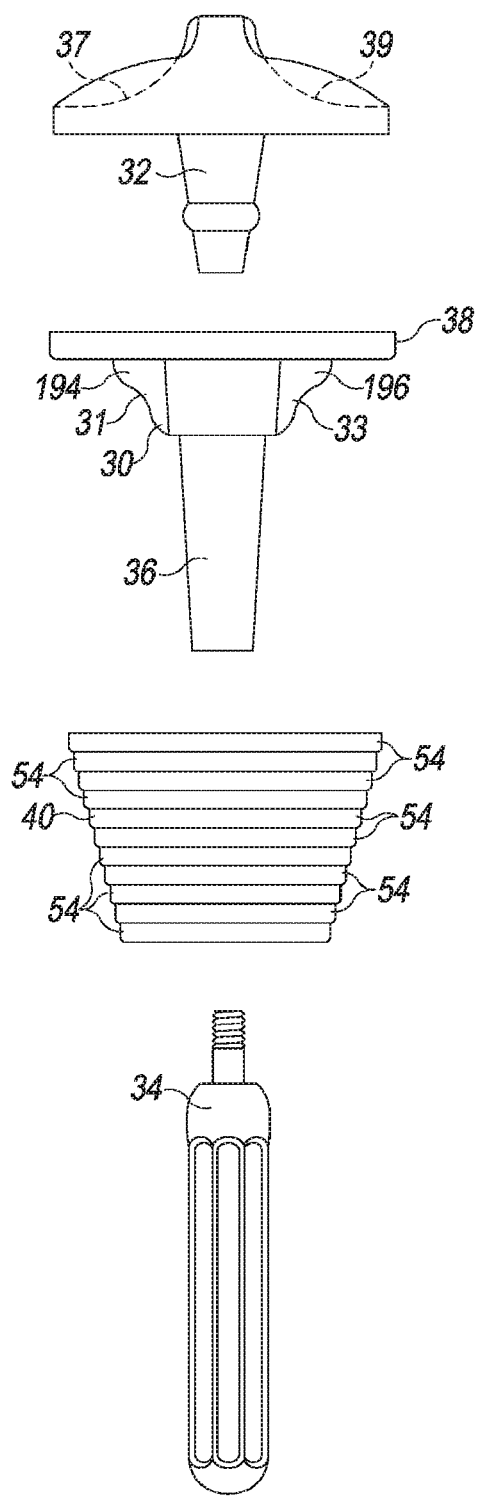
FIG. 2 is a view of the tibial components of a modular knee prosthesis system.

As illustrated in FIG. 2, on the tibial side, the kit includes a tibial tray component 30, a tibial bearing insert 32 and a stem extension 34. The illustrated tibial tray component 30 is a commercial MBT Revision tibial tray, available from DePuy Orthopaedics, Inc. of Warsaw, Ind. The tray component 30 has an integral stem portion 36 with a bore (not shown) with internal threads to which the stem extension 34 may be attached. The outer surface of the stem portion 36 has a smooth finish, tapers away from the joint motion surface and is connected to the inferior surface of the tibial tray component 30 through keels 31, 33. The stem portion 36 extends distally from a platform 38, which has a proximal surface on which the tibial bearing insert 32 rests. The tibial components may also include one or more types or sizes of metaphyseal sleeves, such as sleeve 40 that has a tapered bore (not shown) sized and shaped to frictionally lock with the tapered stem portion 36 of the tibial tray component 30. It should be understood that these tibial components are described for purposes of illustration only; the present invention is not limited to any particular type of tibial component or stem or any other particular component unless expressly called out in the claims. For example, the tibial component may comprise a unitary, all-polymer component or a fixed bearing system, such as those disclosed in U.S. Pat. Nos. 7,628,818 and 8,128,703 (which are incorporated by reference herein in their entireties).

The juncture of the curved convex condyles 12, 14 of the distal femoral component 10 and the curved concave condylar surfaces of the tibial bearing insert 32 (the curved concave condylar surfaces of the tibial bearing insert being shown in FIG. 2 in phantom at 37, 39) define the articulation of the femoral and tibial components as the knee flexes and extends. When the patient's leg is in extension, the contact between the curved convex condyles 12, 14 and concave condylar surfaces 37, 39 corresponds with a distal joint line. As the knee is flexed from full extension, the distal femoral component 10 and tibial bearing insert 32 move with respect to each other so that the joint line at full flexion (when the posterior surfaces of the femoral condyles contact the bearing surface) may vary somewhat from the distal joint line. The plane of the joint line, tangent to the point of contact of the condylar surfaces of the distal femoral component on the tibial insert, is shown at 21 in FIGS. 1 and 13 and at 21A in FIG. 14.

It should be understood that a typical modular knee prosthesis system or kit would include multiple sizes of each of the illustrated tibial components 30, 32, 34, 40.

The metaphyseal sleeves 24, 24A, 24B, 24C are designed for use in a bone wherein the condition of the bone requires additional support or fixation in the metaphysis of the bone. Each of the femoral sleeves 24, 24A, 24B, 24C has an outer surface that includes a distal base 47, 47A, 47B, 47C and a stepped portion 49, 49A, 49B, 49C extending proximally from the distal base to the proximal ends 26, 26A, 26B, 26C. Each stepped portion 49, 49A, 49B, 49C has a plurality of adjacent steps or terraces, shown in FIGS. 3-10 at 50A, 50B, 50C and 50D for the femoral sleeves 24, 24A, 24B, 24C and at 54 for the tibial sleeve 40 (FIG. 2). For the femoral sleeves, the stepped outer surfaces taper proximally: the steps 50, 50A, 50B, 50C at the distal ends 56, 56A, 56B, 56C have the largest anterior-posterior and medial-lateral dimensions and the steps 50, 50A, 50B, 50C at the proximal ends 26, 26A, 26B, 26C have the smallest anterior-posterior and medial-lateral dimensions; the intermediate steps gradually become smaller from the distal ends 56, 56A, 56B, 56C toward the proximal ends 26, 26A, 26B, 26C. For the tibial sleeve 40, the outer surface tapers distally: the most distal step has the smallest anterior-posterior and medial-lateral dimensions and the most proximal step has the largest anterior-posterior and medial-lateral dimensions; the intermediate steps gradually become smaller from the proximal end toward the distal end.

It should be understood that the number and size of the steps 50, 50A, 50B, 50C, may vary from the number and size of steps in the illustrated embodiments. For example, the outer surfaces of the metaphyseal sleeves 24, 24A, 24B, 24C, may have steps and be shaped like standard commercially available metaphyseal sleeves sold by DePuy Orthopaedics, Inc. of Warsaw, Ind., and may be configured like the sleeves disclosed in the prior art, such as, for example, U.S. Pat. No. 7,799,085. The outer surfaces of the sleeves 24, 24A, 24B, 24C, may also be porous coated to promote bone ingrowth, as disclosed in the prior art; the porous coating may extend over substantially all or a portion of the stepped outer surfaces of the sleeves 24, 24A, 24B, 24C.

As shown in FIGS. 1, 3-6 and 11-12, the illustrated femoral sleeves 24, 24A, 24B, 24C have interior surfaces 64, 64A, 64B, 64C defining a proximal bore 68, 68A, 68B, 68C and a distal bore 72, 72A, 72B, 72C. The proximal and distal bores 68, 68A, 68B, 68C, 72, 72A, 72B, 72C in each femoral sleeve may be connected and aligned along central longitudinal axes 76, 76A, 76B, 76C of the bores.

The proximal bores 68, 68A, 68B, 68C of the femoral sleeves 24, 24A, 24B, 24C are sized and shaped to receive a distal end 80 of a stem extension 22. Accordingly, for a stem extension having a Morse taper post at its distal end, the proximal bore would comprise a Morse taper bore sized and shaped to receive and frictionally lock with the Morse taper post. Alternatively, for a stem extension having a threaded distal end, the proximal bore may be threaded to receive and lock to the threaded distal end of the stem extension. An adapter to allow for use of different types of stem extensions may also be used, as disclosed in U.S. Pat. No. 7,799,085.

The distal bores 72, 72A, 72B, 72C of the femoral metaphyseal sleeves 24, 24A, 24B, 24C are frusto-conical Morse taper bores, tapering from the distal ends 56, 56A, 56B, 56C of the sleeves 24, 24A, 24B, 24C toward the proximal ends 26, 26A, 26B, 26C of the sleeves 24, 24A, 24B, 24C. These distal bores 72, 72A, 72B, 72C are sized, shaped and finished to be mountable on the stem or adapter 16 of the distal femoral component 10 and to create a frictional lock between the stem of the distal femoral component and the metaphyseal sleeve, the stem or adapter 16 defining a Morse taper post.

As used herein, "Morse taper" refers to one type of locking tapers between mating components. Generally, Morse taper posts and bores have frusto-conical shapes, substantially the same taper angle and have complementary outer and inner diameters at some point along their length to allow for tight frictional engagement between the posts and the walls defining the bores. Standard taper angles and standard surface finishes for such locking tapers may be used in the present invention. It should be appreciated that other types of tapered components may be used.

In the illustrated knee prosthesis system, the distal bores 72, 72A, 72B, 72C of each size of sleeve 24, 24A, 24B, 24C has the same maximum inner diameter at the distal end 56, 56A, 56B, 56C of the sleeve. This maximum inner diameter substantially corresponds with the maximum outer diameter of the tapered frusto-conical outer surface 75 of the stem or adapter 16 of the distal femoral component 10. The distal bores 72, 72A, 72B, 72C of all the sizes of sleeves 24, 24A, 24B, 24C and the tapered frusto-conical outer surface 75 of the stem or adapter 16 taper in the proximal direction at substantially the same taper angle so that relative axial movement of the sleeve 24, 24A, 24B, 24C and stem or adapter 16 locks the two together when the interior surface 64, 64A, 64B, 64C of the sleeve 24 engages and frictionally locks with the tapered frusto-conical outer surface 75 of the stem or adapter 16.

Figure 3:
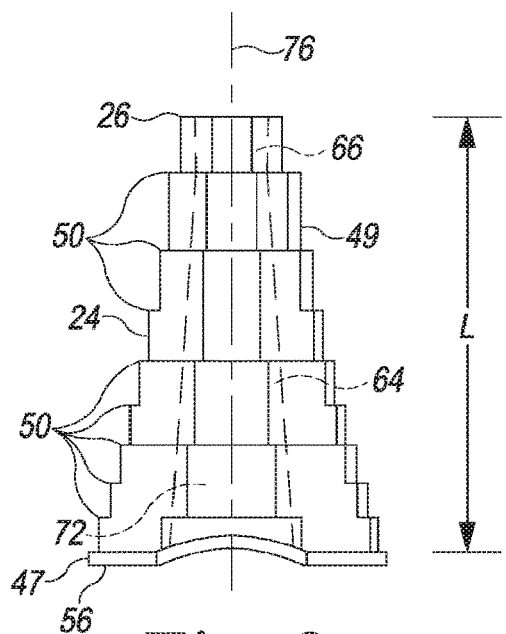
FIG. 3 is a medial-lateral view of the smallest size of metaphyseal sleeves of the modular knee prosthesis system of FIG. 1.
Figure 4:
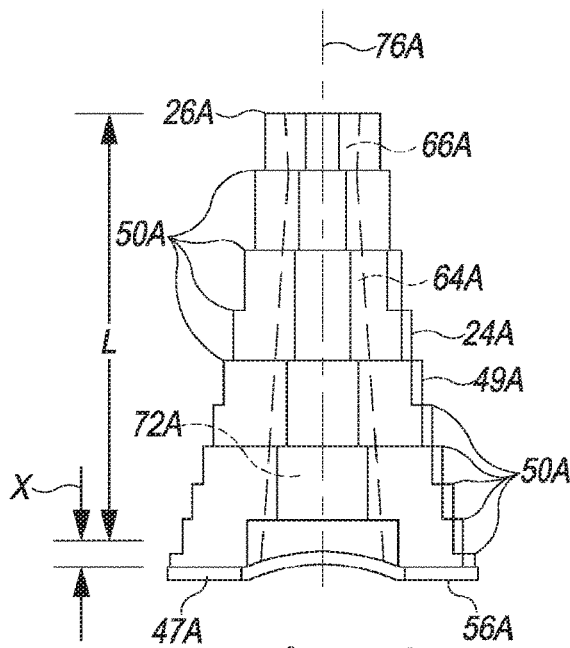
FIG. 4 is a medial-lateral view of another size of metaphyseal sleeves of the modular knee prosthesis system of FIG. 1.
Figure 5:
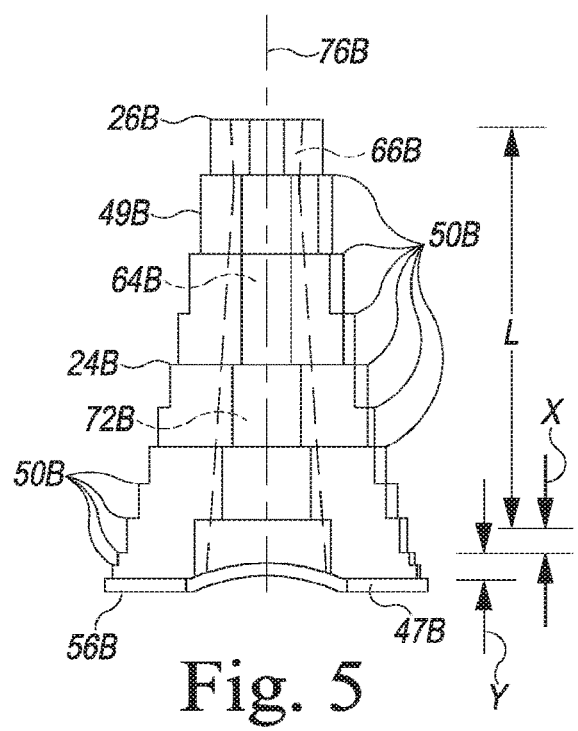
FIG. 5 is a medial-lateral view of another size of metaphyseal sleeves of the modular knee prosthesis system of FIG. 1.
Figure 6:
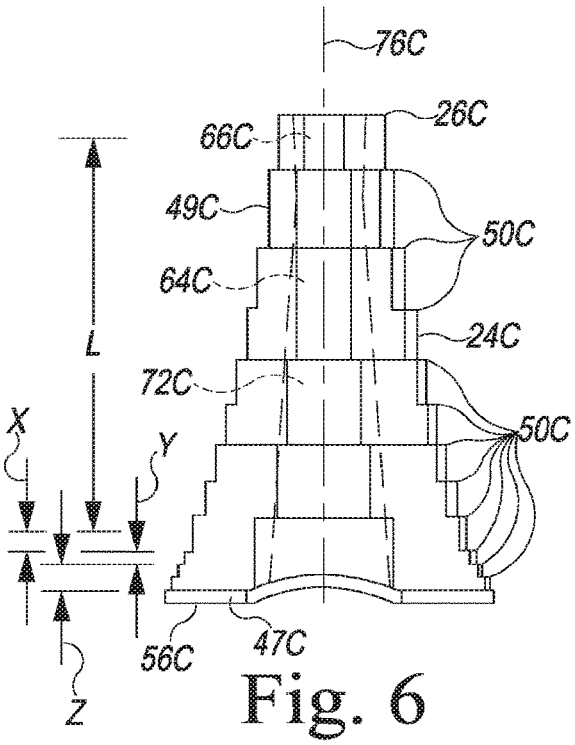
FIG. 6 is a medial-lateral view of the largest size of metaphyseal sleeves of the modular knee prosthesis system of FIG. 1.
Figure 7:
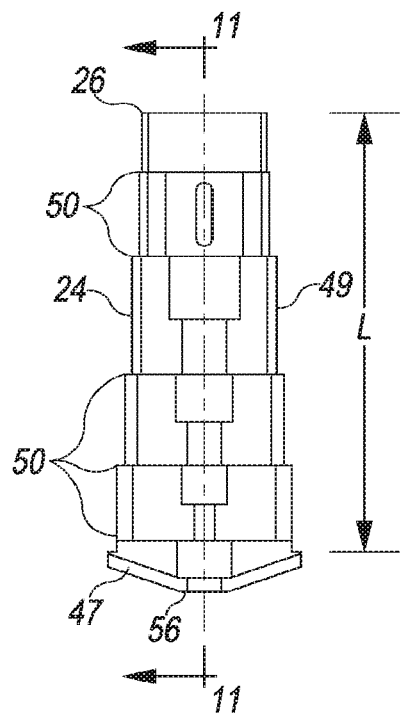
FIG. 7 is an anterior-posterior view of the metaphyseal sleeve of FIG. 3.
Figure 8:
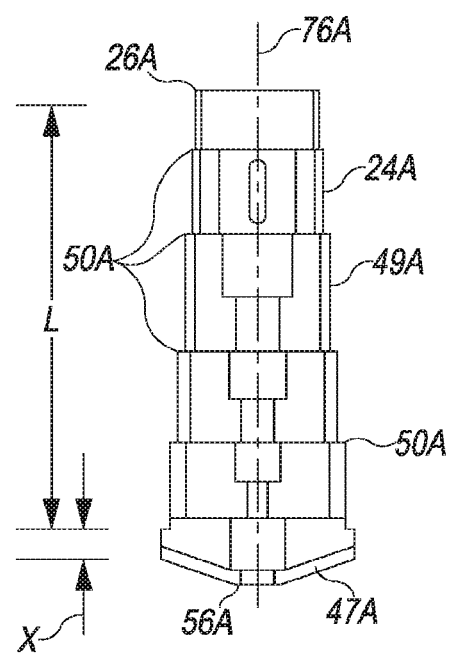
FIG. 8 is an anterior-posterior view of the metaphyseal sleeve of FIG. 4.
Figure 9:
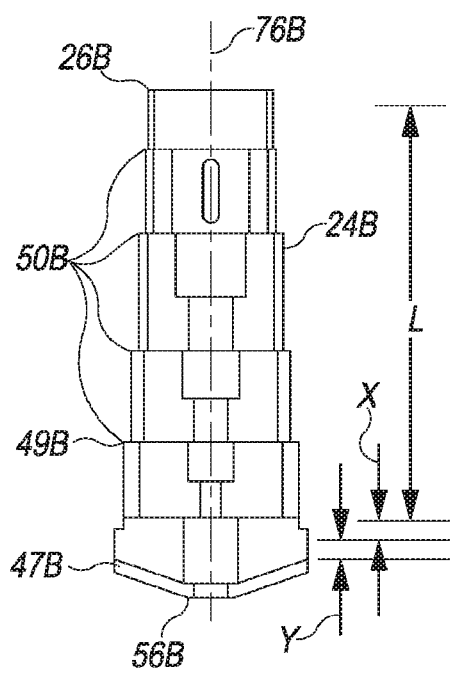
FIG. 9 is an anterior-posterior view of the metaphyseal sleeve of FIG. 5.
Figure 10:
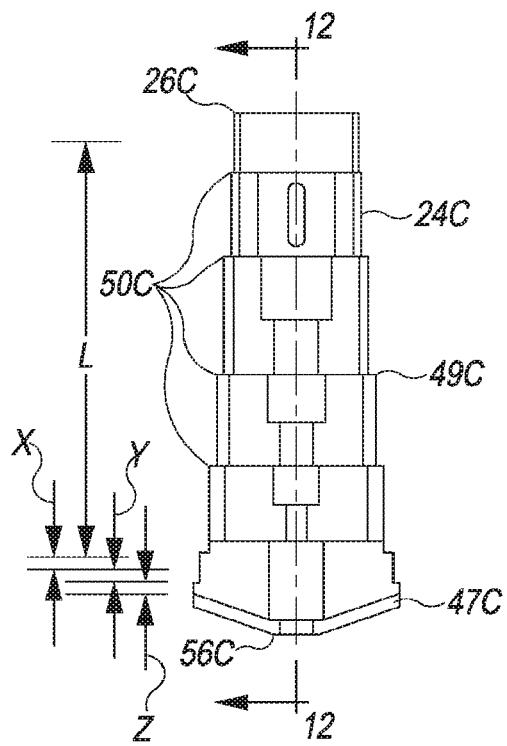
FIG. 10 is an anterior-posterior view of the metaphyseal sleeve of FIG. 6.
Figure 11:
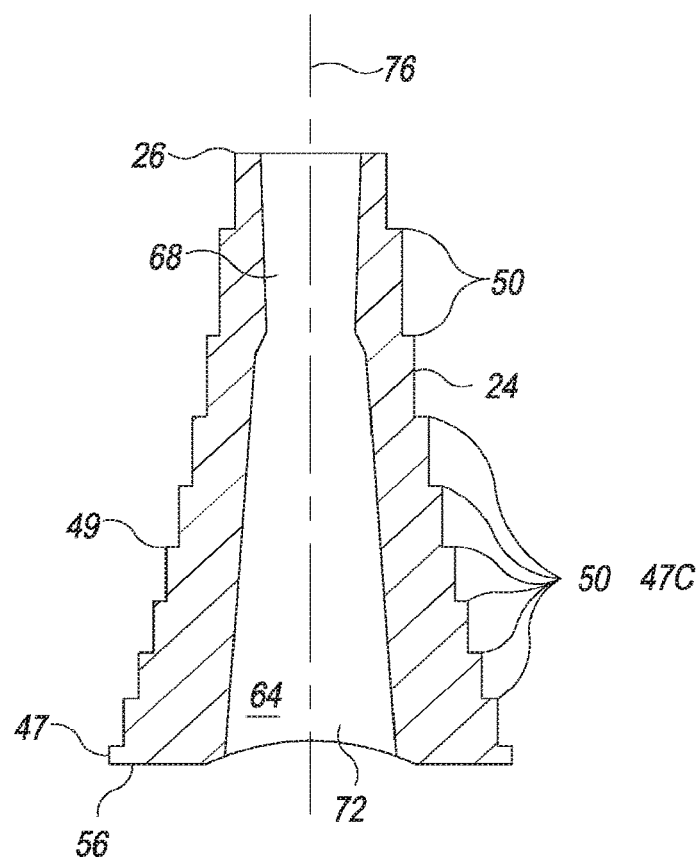
FIG. 11 is a cross-sectional view of the metaphyseal sleeve of FIG. 7, taken along line 11-11 of FIG. 7.
Figure 12:
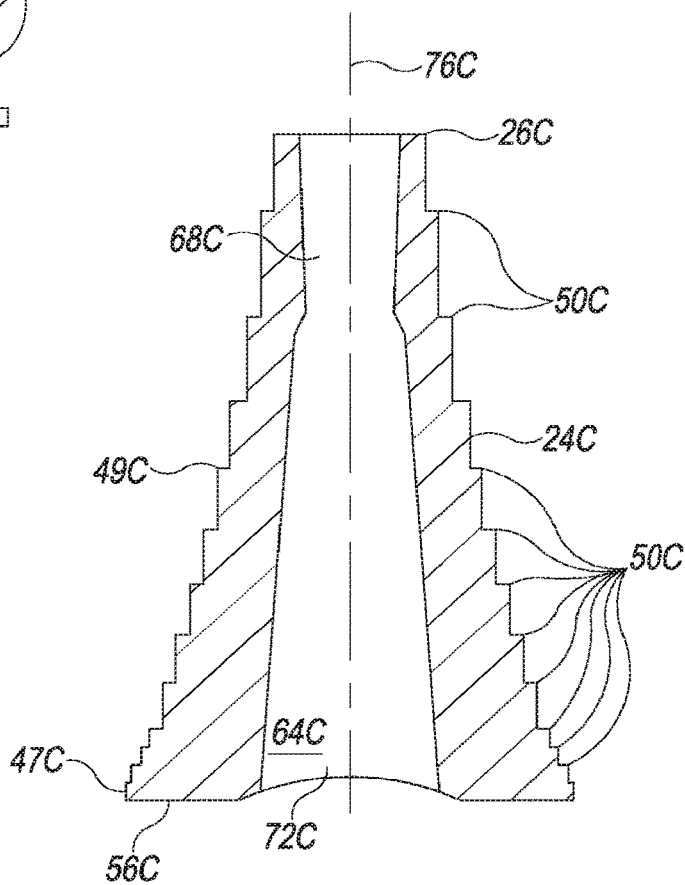
FIG. 12 is a cross-sectional view of the metaphyseal sleeve FIG. 10, taken along line 12-12 of FIG. 10.
Figure 13:
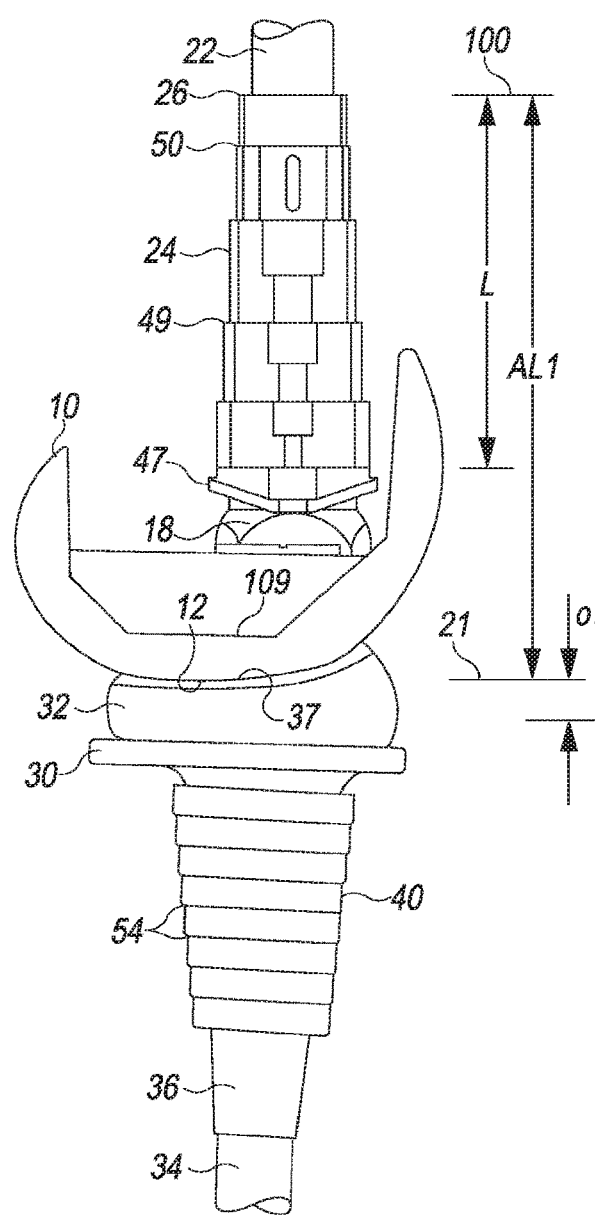
FIG. 13 is an anterior-posterior view of a modular knee prosthesis system using a standard femoral stem and the smallest size of metaphyseal sleeve.

As shown in FIGS. 3, 7 and 13, the stepped outer surface 49 of the smallest size of femoral metaphyseal sleeve 24 has an overall axial length between the distal base 47 and the proximal end 26 shown at "L". The stepped outer surface 49A of the next larger size of femoral metaphyseal sleeve 24A has an overall axial length between the base 47A and the proximal end 26A of "L+X", the dimensions "L" and "X" being shown in FIGS. 4 and 8. The stepped outer surface 49B of the next larger size of femoral metaphyseal sleeve 24B has an overall axial length between the base 47B and the proximal end 26B of "L+X+Y", the dimensions "L", "X" and "Y" being shown in FIGS. 5 and 9. The stepped outer surface 49C of the largest illustrated size of femoral metaphyseal sleeve 24C has an overall axial length between the base 47C and the proximal end 26C of "L+X+Y+Z", the dimensions "L", "X", "Y" and "Z" being shown in FIGS. 6, 10 and 14. The different sizes of femoral metaphyseal sleeves may be provided with differences of a few millimeters (for example, 4 millimeters) between each size, so that X=4 mm, Y=4 mm and Z=4 mm. It should be understood that these dimensions are provided as examples only; the inventions is not limited to any particular dimensions unless expressly called for in the claims.

In the illustrated modular knee prosthesis system, the geometries of the stepped outer surfaces 49, 49A, 49B, 49C of all sizes of femoral metaphyseal sleeve 24, 24A, 24B, 24C are essentially identical over axial length "L". Thus, if "L" is 68 mm for the smallest sleeve, the sizes and shapes of the proximal 68 mm of the other sleeve sizes 24A, 24B, 24C are essentially identical to the size and shape of the proximal 68 mm of the smallest sleeve 24. In other words, over axial length "L" for all of the illustrated sizes of femoral metaphyseal sleeves 24, 24A, 24B, 24C, the sleeves have the same number of steps, and each step has the same maximum medial-lateral dimension, the same maximum anterior-posterior dimension, the same axial height and the same shape. The different sizes of femoral metaphyseal sleeves differ only in the sizes of the bases 47, 47A, 47B, 47C and in the distal portions corresponding with the axial extensions of the sleeves beyond the length "L" of the smallest sleeve 24.

| Femoral Sleeve | Maximum A-P Dimension at "L" | Maximum A-P Dimension distal to "L" | Maximum M-L Dimension at "L" | Maximum M-L Dimension distal to "L" |
|---|---|---|---|---|
| 24 | 22 mm | Not applicable | 34 mm | Not applicable |
| 24A | 22 mm | 24 mm | 34 mm | 40 mm |
| 24B | 22 mm | 24 mm | 34 mm | 46 mm |
| 24C | 22 mm | 26 mm | 34 mm | 52 mm |

Figure 14:
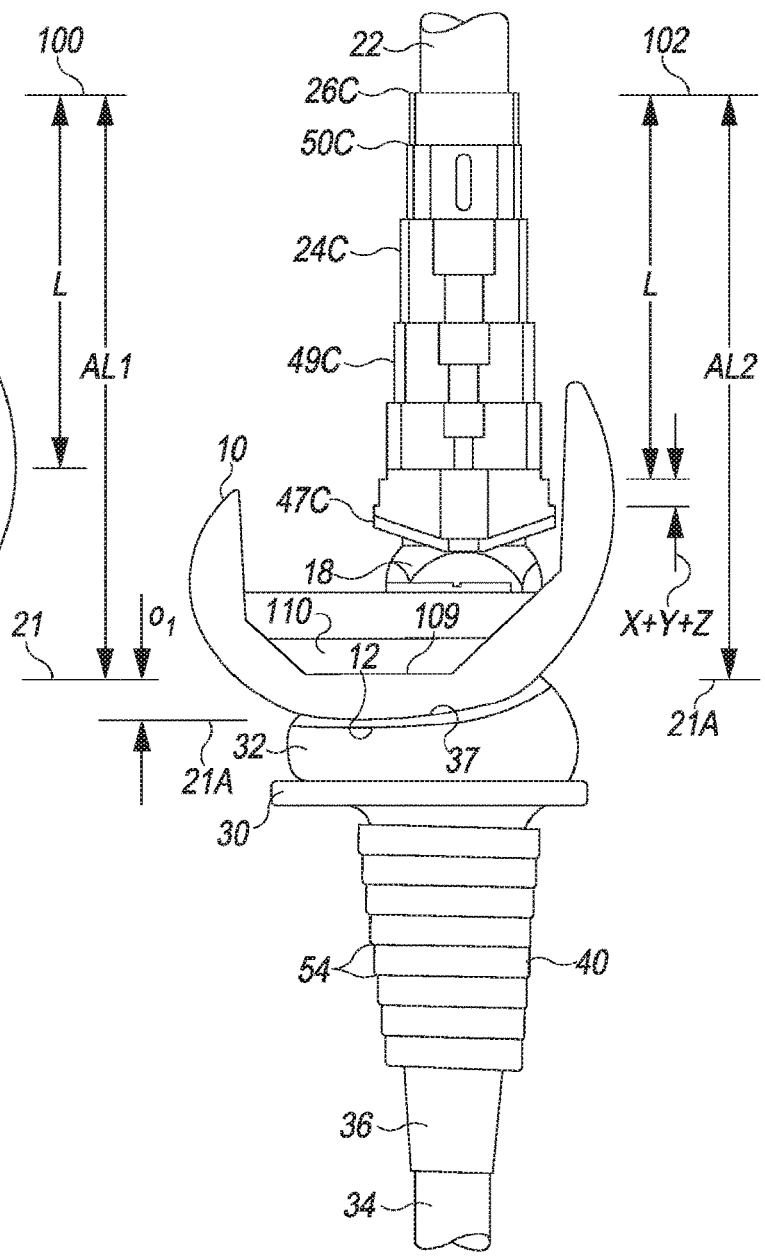
FIG. 14 is an anterior-posterior view of a modular knee prosthesis system similar to FIG. 13 but shown with the largest size of metaphyseal sleeve.

FIGS. 13 and 14 illustrate assemblies of the smallest and largest illustrated femoral metaphyseal sleeves 24, 24C with a distal femoral implant component 10, femoral stem extension 22, tibial tray 30, tibial insert 32 and tibial stem extension 34. The illustrated assemblies have maximum axial lengths from planes at the proximal ends 26, 26C (the planes shown at 100 and 102) to the plane of the joint line, shown at 21 in FIG. 13 and at 21A in FIG. 14. These maximum axial lengths of the assemblies are shown at AL1 in FIG. 13 and AL2 in FIG. 14. AL2 is longer than AL1 by the dimension "X+Y+Z", that is the axial length of the sleeve 24C beyond the length "L" of the smallest sleeve 24.

As can also be seen from a comparison of FIGS. 13 and 14, using the larger sleeve 24C distalizes the joint line 21 to the position 21A by the offset distance $o_1$. This offset distance $o_1$ also corresponds with the dimension "X+Y+Z". Similarly, using the sleeve 24A distalizes the joint line by the dimension "X" and using the sleeve 24B distalizes the joint line by the dimension "X+Y".

Since the geometries of the stepped outer surfaces 49, 49A, 49B, 49C of the different sizes of sleeves 24, 24A, 24B, 24C are the same through axial length "L", the surgeon can prepare the distal femur to receive the smallest size of femoral sleeve 24. If the surgeon determines intraoperatively that the joint line should be distalized, the surgeon may use any of the other sizes of sleeve 24A, 24B, 24C, and the proximal portion of the larger size sleeve will fit within the opening prepared in the femur to receive the smaller sleeve and extend distally from the bone by the distance "X", "X+Y" or "X+Y+Z" to thereby distally offset the joint line. The surgeon can accomplish this distalization without any further preparation of the bone cavity.

As described above, femoral augments may be used on the distal and posterior bone-facing surfaces of the femoral implant components when the joint line is distalized. In the illustrative embodiment, a distal augment 110 may be attached to one of a pair of distal fixation surfaces 109 of the distal femoral implant component 10 when the sleeve 24C is used, as shown in FIG. 14. In the illustrative embodiment, the thickness of the augment 109 is equal to the offset distance $o_1$. One of the distal fixation surfaces 109 is positioned opposite the condylar surface 12 and the other distal fixation surface 109 is positioned opposite the condylar surface 14. It should be appreciated that another distal augment may be attached to that surface as well. When the sleeve 24 is used, no augment is necessary, as shown in FIG. 13.

It should also be appreciated that the principles of the present invention may also be applied to the tibial components of the knee implant system, such as the tibial sleeve 40 shown in FIG. 2. Such a system could allow the surgeon to select components to provide a proximal offset to the tibial tray platform 38.

All of the components of the prosthesis systems described herein may be made of standard materials, such as a standard polymer (UHMWPE, for example) for the tibial bearing insert 32 and standard metals, such as cobalt-chromium and titanium alloys, for the remaining components. To promote bone ingrowth, the sleeves 24, 24A, 24B, 24C may be porous coated, or could comprise titanium foam as disclosed in U.S. Pat. Pub. Nos. 20100057212 ("Porous Titanium Tibial Sleeves and Their Use in Revision Knee Surgery") and 20100076565 ("Porous Titanium Femoral Sleeves and Their Use in Revision Knee Surgery"), both of which are incorporated by reference herein in their entireties.

Referring now to FIGS. 15-37, another modular knee prosthesis system is shown with different embodiments of the femoral components (hereinafter components 200). An orthopaedic surgical instrument system 300 for use with the modular knee prosthesis system is also shown. Some features of the embodiments illustrated in FIGS. 15-37 are substantially similar to those discussed above in reference to the embodiment of FIGS. 1-14. Such features are designated in FIGS. 15-37 with the same reference numbers as those used in FIGS. 1-14.

Figure 15:
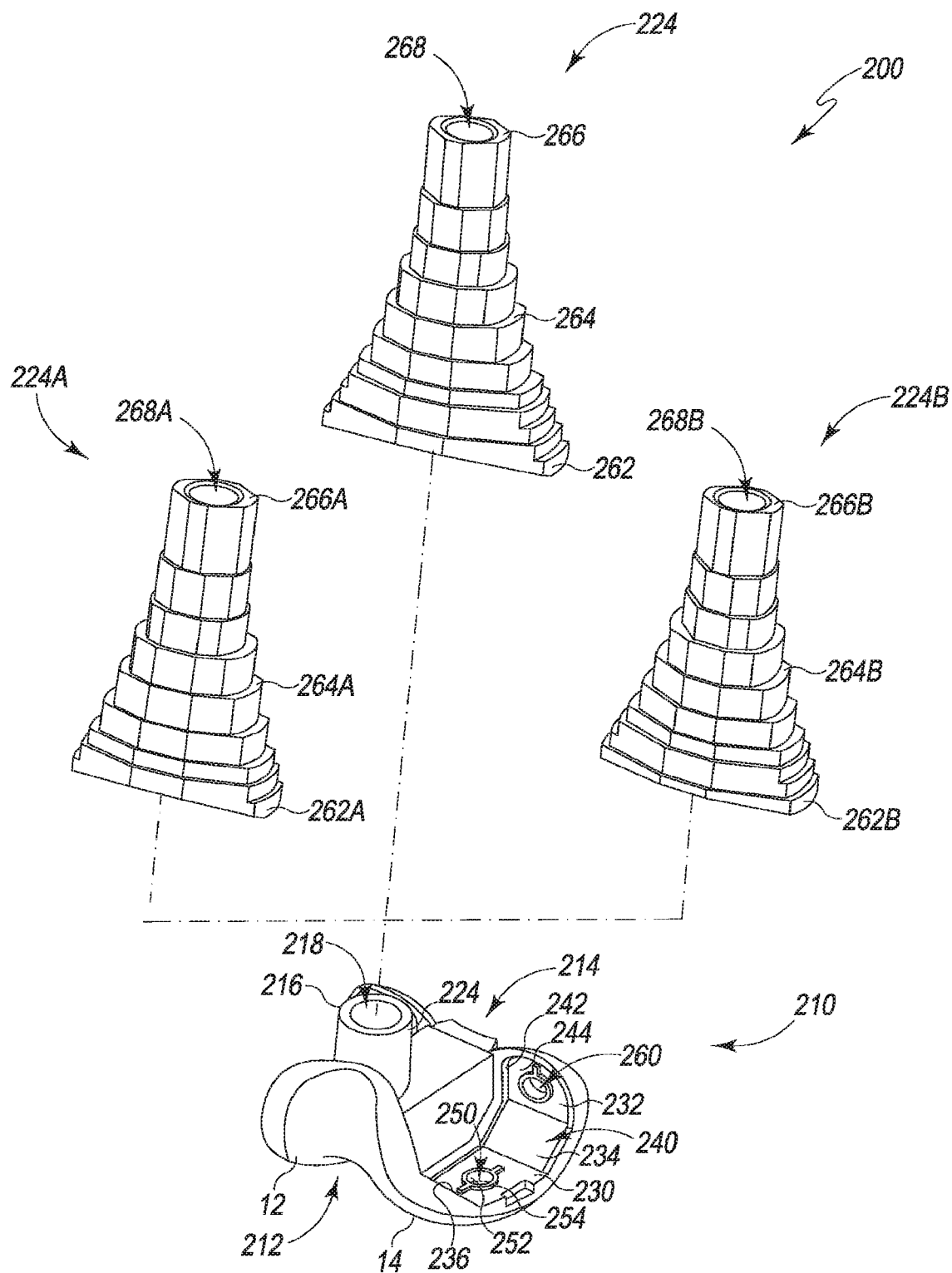
FIG. 15 is a view of another embodiment of a modular prosthesis system.

As shown in FIG. 15, the femoral components 200 of the system include a femoral component 210 including distal curved convex condylar surfaces 12, 14. The surfaces 12, 14 are shaped (i.e., curved) in a manner that approximates the condyles of the natural femur. In the illustrative embodiment, the condylar surface 12 is a medial condyle surface 12, and the condylar surface 14 is a lateral condyle surface 14. The surfaces 12, 14 are spaced apart from one another, thereby defining an intercondylar notch therebetween.

The condyle surfaces 12, 14 are formed in a bearing surface 212 of the femoral component 210, and the femoral component 210 includes a fixation surface 214 positioned opposite the bearing surface 212. The femoral component 210 also includes an elongated stem post 216 that extends superiorly away from the surface 214. The elongated stem post 216 is configured to receive a stem component such as, for example, the stem extension 22, or engage a metaphyseal sleeve such as, for example, the sleeves 24, 24A, 24B, 24C described above or sleeves 224, 224A, 224B, which are described in greater below.

Specifically, as shown in FIG. 15, the elongated stem post 216 of the femoral component 210 has a tapered bore 218 defined therein into which the tapered distal end 80 of the stem extension 22 may be advanced to taper lock the post 216 to the stem extension 22. Similar to the adaptor 16 of the distal femoral component 10, the outer surface 220 of the elongated stem post 216 is also tapered and may be advanced into one of the distal bores 72, 72A, 72B, 72C of the sleeves 24, 24A, 24B, 24C, respectively, or one of the tapered distal bores 272, 272A, 272B of the sleeves 224, 224A, 224B. As described above, each distal bore is shaped and finished to create a frictional lock such as, for example, a taper lock, between the corresponding sleeve and the femoral component 210. In the illustrative embodiment, the outer surface 220 defines a Morse taper.

The fixation surface 214 of the femoral component 210 includes a number of surfaces 230, 232, 234, 236 positioned opposite the condyle surfaces 12, 14. In the illustrative embodiment, the fixation surface 214 includes a pair of distal fixation surfaces 230 similar to the distal fixation surface 109 of distal femoral component 10. One of the distal fixation surfaces 230 is positioned medially and the other is positioned laterally. The fixation surface 214 also includes a pair of posterior fixation surfaces 232, with one being medially positioned and the other laterally positioned. As shown in FIG. 15, the posterior fixation surfaces 232 extend generally in the superior/inferior direction.

The fixation surface 214 also includes a pair of posterior chamfer surfaces 234, with one being medially positioned and the other laterally positioned. The medial and lateral posterior-chamfer fixation surfaces 234 extend superiorly and posteriorly from their respective lateral and medial distal fixation surfaces 230 to their respective posterior fixation surfaces 232. As shown in FIG. 15, the fixation surface 214 has a pair of anterior chamfer surfaces 236, with one being medially positioned and the other laterally positioned. The medial and lateral anterior-chamfer fixation surfaces 236 extend superiorly and posteriorly from their respective lateral and medial distal fixation surfaces 230 to their respective posterior fixation surfaces 232.

Each of the fixation surfaces 230, 232, 234, 236 has a cement pocket formed therein. In the illustrative embodiment, the cement pockets are contiguous with one another such that a single, continuous cement pocket 240 is formed in both the medial and lateral fixation surfaces 214 of the femoral component 210. Each cement pocket 240 is defined by a side wall 242 that extends inwardly from the respective fixation surface 214 to a bottom wall 244.

A mounting aperture 250 is defined in each distal fixation surface 230. As shown in FIG. 15, the aperture 250 is defined by a cylindrical wall 252 that extends inwardly from a rim 254 positioned in the cement pocket 240. As described in greater detail below, the aperture 250 is sized to receive a mounting plug 256 of a distal augment component 342, 344 to secure the augment component 342, 344 to the femoral component 210.

Another mounting aperture 260 is defined in each posterior fixation surface 232. As shown in FIG. 15, the aperture 260 is defined by a cylindrical wall 252 that extends inwardly from a rim 254 positioned in the cement pocket 240. As described in greater detail below, the aperture 260 is sized to receive a mounting plug 256 of a posterior augment component 346, 348 to secure the augment component 346, 348 to the femoral component 210.

As shown in FIG. 15, the femoral components 200 include a plurality of sizes of metaphyseal sleeves 224, 224A, 224B. Similar to the sleeves 24, 24A, 24B, 24C described above, the geometries of the sleeves 224, 224A, 224B of the exterior surfaces of the three sizes are the same over a portion of their axial lengths. As used herein, the terms "same," "match," or "identical" refer to components that are designed to have the same dimensions and configuration. Such components may be subject to accepted tolerances or manufacturing variations that cause the components to vary slightly in some respect. For example, the portions of metaphyseal sleeves 224, 224A, 224B that are designed to be the same may nevertheless vary slightly due to manufacturing tolerances. Nevertheless, such components are the same, match, or are identical because they are designed to have the same configuration and dimensions. It should be understood that multiple sizes of femoral components 210 would typically be included in the modular knee prosthesis system. It should also be understood that a modular knee prosthesis system utilizing the principles of the present disclosure may include fewer or more sizes of metaphyseal sleeves 224, 224A, 224B.

Similar to the sleeves 24, 24A, 24B, 24C, the sleeves 224, 224A, 224B are designed for use with bones in which the condition of the bone requires additional support or fixation in the metaphysis of the bone. As shown in FIG. 15, each of the sleeves 224, 224A, 224B has a distal base 262, 262A, 262B and a body 264, 264A, 264B extending proximally from its respective distal base to a respective proximal end 266, 266A, 266B.

As shown in FIG. 15, each of the sleeves 224, 224A, 224B has a proximal bore 268, 268A, 268B defined in the proximal end 266, 266A, 266B thereof. The proximal bores 268, 268A, 268B, of the femoral sleeves 224, 224A, 224B are sized and shaped to receive a distal end 80 of a stem extension 22. Accordingly, for a stem extension having a tapered post at its distal end, the proximal bore would comprise a tapered bore sized and shaped to receive and frictionally lock with the tapered post. Alternatively, for a stem extension having a threaded distal end, the proximal bore may be threaded to receive and lock to the threaded distal end of the stem extension. As described above, each of the sleeves 224, 224A, 224B has a distal bore 272, 272A, 272B, which is defined in the respective distal base 262, 262A, 262B of each sleeve, as shown in FIGS. 16-18.

Referring now to FIGS. 16-18, the bodies 264, 264A, 264B of the sleeves 224, 224A, 224B include a plurality of stepped walls 274, 274A, 274B. Each pair of adjacent stepped walls 274, 274A, 274B is connected by an annular surface 276, 276A, 276B. As a result, the bodies 264, 264A, 264B are terraced similar to the sleeves 24, 24A, 24B, 24C. In the illustrative embodiment, the bodies 264, 264A, 264B are tapered such that the sleeves 224, 224A, 224B have the smallest anterior-posterior dimensions and the smallest medial-lateral dimensions at their respective proximal ends 266, 266A, 266B and become progressively larger as the bodies 264, 264A, 264B extend to their respective distal bases 262, 262A, 262B.

It should be understood that the number and size of the stepped walls 274, 274A, 274B may vary from the number and size of steps in the illustrated embodiments. The outer surfaces of the sleeves 262, 262A, 262B may also be porous coated to promote bone ingrowth, as disclosed in the prior art; the porous coating may extend over substantially all or a portion of the stepped outer surfaces of the sleeves 224, 224A, 224B. It should be understood that these dimensions are provided as examples only; the disclosure is not limited to any particular dimensions unless expressly called for in the claims.

As shown in FIG. 16, the body 264 of the sleeve 224 has a longitudinal axis 280 and a tapered outer surface 282 that has an axial length "L" defined along the axis 280. In the illustrative embodiments, the annular surfaces 276 are substantially flat. As a result, the stepped walls 274 combine to define the axial length L of the body 264. In the illustrative embodiment, the axial length L is equal to approximately 45 millimeters.

As shown in FIG. 17, the body 264A of the sleeve 224A has a longitudinal axis 280A and a tapered outer surface 282A. The tapered outer surface 282A has a proximal section 284A that has an axial length "L" defined along the axis 280A and a section 286A extending distally from the proximal section 284A to the distal base 262A. The section 286A has an axial length "X" defined along the axis 280A. As a result, the overall axial length of the body 264A is "L+X." In the illustrative embodiment, the axial length "L+X" is equal to approximately 50 millimeters.

As shown in FIG. 18, the body 264B of the sleeve 224B has a longitudinal axis 280B and a tapered outer surface 282B. The tapered outer surface 282B has a proximal section 284B that has an axial length "L" defined along the axis 280B and a section 286B extending distally from the proximal section 284A. The section 286A has an axial length "X" defined along the axis 280B. The tapered outer surface 282B has another section 288B that extends distally from the section 286B to the distal base 262B. The section 288B has an axial length "Y" defined along the axis 280B. As a result, the overall axial length of the body 264A is "L+X+Y." In the illustrative embodiment, the axial length "L+X+Y" is equal to approximately 55 millimeters.

In the illustrative embodiment, the different sizes of femoral metaphyseal sleeves may be provided with differences of a few millimeters (for example, 5 millimeters) between each size, so that X=5 mm, Y=5 mm and Z=5 mm. Additionally, the overall axial length of the different sleeves may vary. For example, in one embodiment, the overall axial lengths of the sleeves may be between 30 millimeters and 55 millimeters.

In the illustrated modular knee prosthesis system, the outer geometries of the tapered outer surfaces 282, 282A, 282B of all sizes of femoral metaphyseal sleeve 224, 224A, 224B are essentially identical over axial length "L." Thus, if "L" of the sleeve 224 is 45 mm, the sizes and shapes of the proximal 45 mm of the other sleeve sizes 224A, 224B (i.e., the proximal sections 284A, 284B) are essentially identical to the size and shape of the proximal 45 mm of the sleeve 224. In other words, over axial length "L" for all of the illustrated sizes of femoral metaphyseal sleeves 224, 224A, 224B, the sleeves have the same number of stepped walls, as shown in FIGS. 16-18. Further, as shown in FIG. 19, each stepped wall over axial length "L" also has the same maximum medial-lateral dimension 290, the same maximum anterior-posterior dimension 292, and the same shape. Each stepped wall over axial length "L" also has the same axial height, as shown in FIGS. 16-18.

The different sizes of femoral metaphyseal sleeves 224, 224A, 224B differ only in the sizes of the bases 262, 262A, 262B and in the distal portions corresponding with the axial extensions of the sleeves beyond a given axial length. For example, the tapered outer surfaces 282A, 282B of the femoral metaphyseal sleeve 224A, 224B are essentially identical over axial length "X." Thus, if "X" of the sleeve 224A is 5 mm, the size and shape of the section 286B of the sleeve 224B is essentially identical to the size and shape of the section 286A of the sleeve 224A. In other words, over axial length "X" for the illustrated sizes of femoral metaphyseal sleeves 224A, 224B, the sleeves have the same number of stepped walls, as shown in FIGS. 17-18. Further, as shown in FIG. 20, each stepped wall has the same maximum medial-lateral dimension 294, the same maximum anterior-posterior dimension 296, and the same shape. Nevertheless, the femoral metaphyseal sleeve 224B differs from the sleeve 224A in the size of the base 262B and in the configuration of the distal section 288B.

Referring now to FIGS. 21-25, a plurality of surgical instruments 300, which may be used with the femoral components 200, is shown. In the illustrative embodiment, the surgical instruments 300 are a plurality of sizes of surgical broaches 302, 302A, 302B. Each of the broaches 302, 302A, 302B is formed from a metallic material such as, for example, stainless steel or cobalt chromium. As described in greater detail below, the outer geometries of the broaches 302, 302A, 302B are the same over a portion of their axial lengths and correspond to the outer geometries of the metaphyseal sleeves 224, 224A, 224B. As described above, in other embodiments, the femoral components 200 may include fewer or more sizes of metaphyseal sleeves 224, 224A, 224B; it should be appreciated that in such embodiments the surgical instruments 300 may include fewer or more sizes of broaches 302, 302A, 302B.

Each of the broaches 302, 302A, 302B includes a proximal tip 304, 304A, 304B and a body 306, 306A, 306B extending from the proximal tip 304, 304A, 304B to a respective distal end 308, 308A, 308B. In the illustrative embodiment, the tip 304, 304A, 304B of each broach 302, 302A, 302B has an aperture 310, 310A, 310B defined therein that is sized to receive a femoral stem trial. The distal end 308, 308A, 308B of each broach 302, 302A, 302B is configured to engage an attachment mechanism of an instrument handle. An exemplary configuration of the distal end 308, 308A, 308B of each broach 302, 302A, 302B is shown and described in U.S. patent application Ser. No. 13/834,862 entitled "FEMORAL SYSTEM HANDLE SURGICAL INSTRUMENT AND METHOD OF ASSEMBLING SAME", which was filed concurrently herewith and is expressly incorporated herein by reference.

The bodies 306, 306A, 306B have a plurality of cutting teeth 312, 312A, 312B defined in the outer surface 322, 322A, 322B thereof. The cutting teeth 312, 312A, 312B are configured to engage the bone surrounding the medullary canal of the patient's femur to define a cavity in the bone sized to receive a sleeve. The cutting teeth 312, 312A, 312B cooperate to define a plurality of stepped planes 314, 314A, 314B of their respective outer surfaces 322, 322A, 322B. As a result, the bodies 264, 264A, 264B are terraced. In the illustrative embodiment, the bodies 306, 306A, 306B are tapered such that the broaches 302, 302A, 302B have the smallest anterior-posterior dimensions and the smallest medial-lateral dimensions at their respective proximal tips 304, 304A, 304B and become progressively larger as the bodies 306, 306A, 306B extend to their respective distal ends 308, 308A, 308B. In the illustrative embodiment, the number of stepped planes 314, 314A, 314B of the broaches 302, 302A, 302B corresponds to the number of the stepped walls 274, 274A, 274B of the sleeves 224, 224A, 224B, respectively.

As shown in FIG. 21, the body 306 of the broach 302 has a longitudinal axis 320 and a tapered outer surface 322 defined by the tips 324 of the cutting teeth 312. The tapered outer surface 322 has an axial length "L" defined along the axis 320. In that way, the body 306 has the same axial height as the body 264 of the sleeve 224. Additionally, the stepped planes 314 of the body 306 combine to define the axial length L of the body 306. In the illustrative embodiment, the number of stepped planes 314 is equal to the number of stepped walls 274 of the sleeve 224; as such, each stepped plane 314 corresponds to a stepped wall 274 of the sleeve 224.

The tapered outer surface 322 of the broach 302 has a proximal section 326 extending from the proximal tip 304 and a section 328 extending from the proximal section 326 to the distal end 308. The distal section 328 has an axial length that is approximately 50% of the axial length L.

In the proximal section 326 of the tapered outer surface 322, the outer geometry of the broach 302 defined by the stepped planes 314 is the same as the corresponding outer geometry of the sleeve 224 defined by the stepped walls 274. In other words, the number of stepped planes 314 is equal to the number of stepped walls 274, and each stepped plane 314 has the same maximum medial-lateral dimension, the same maximum anterior-posterior dimension, and the same axial height as the corresponding stepped wall 274. For example, as shown in FIG. 24, the stepped planes 314 in the proximal section 326 define the same maximum medial-lateral dimension 290 and the same maximum anterior-posterior dimension 292 as the corresponding stepped wall 274 of the sleeve 224. As a result, the broach 302 is configured to define a cavity in the patient's femur that includes a proximal section that is substantially the same as the sleeve 224 such that the sleeve 224 is fitted into that section.

In the distal section 328 of the tapered outer surface 322 the number of stepped planes 314 is equal to the number of stepped walls 274, and each stepped plane 314 has the same axial height as the corresponding stepped wall 274. However, the maximum medial-lateral dimension and the maximum anterior-posterior dimension of each stepped plane 314 are smaller than the maximum medial-lateral dimension and the maximum anterior-posterior dimension of the corresponding stepped wall 274. In other words, the outer geometry of the broach 302 defined by the stepped planes 314 is smaller than the corresponding outer geometry of the sleeve 224 defined by the stepped walls 274. As a result, the broach 302 is configured to define a cavity in the patient's femur that includes a distal section that is smaller than the sleeve 224 such that the sleeve 224 is press fit into that section.

In the illustrative embodiment, the maximum medial-lateral dimension of each stepped plane 314 in the distal section 328 is 0.35 mm less than the maximum medial-lateral dimension of the corresponding stepped wall 274 of the sleeve 224. Similarly, the maximum anterior-posterior dimension of each stepped plane 314 in the distal section 328 is 0.35 mm less than the maximum anterior-posterior dimension of the corresponding stepped wall 274 of the sleeve 224. It should be appreciated that in other embodiments the dimensions of the broach 302 may be adjusted to provide greater or less press fit for the sleeve 224.

Furthermore, since the geometries of the outer surfaces 282, 282A, 282B of the femoral metaphyseal sleeves 224, 224A, 224B are essentially identical through axial length "L," the sleeves 224A, 224B will fit within a cavity prepared by the broach 302 in a patient's femur and extend distally from the bone by the distance "X" or "X+Y." As such, if the sleeve 224A is inserted into a cavity prepared by the broach 302, the portion of the sleeve 224 corresponding to the distal section 328 of the broach 302 will be press fit, while the portion corresponding to the proximal section 326 of the broach 302 will be fitted into that portion of the cavity.

As shown in FIG. 22, the body 306A of the broach 302A has a longitudinal axis 320A and a tapered outer surface 322A defined by the tips 324A of the cutting teeth 312A. The tapered outer surface 322A has an axial length "L+X" defined along the axis 320A. In that way, the body 306A has the same axial height as the sleeve 224A. Additionally, the stepped planes 314A of the body 306A combine to define the axial length "L+X" of the body 306A. In the illustrative embodiment, the number of stepped planes 314A is equal to the number of stepped walls 274A of the sleeve 224A; as such, each stepped plane 314A corresponds to a stepped wall 274A of the sleeve 224A.

The tapered outer surface 322A of the broach 302A has a proximal section 326A extending from the proximal tip 304A and a section 328A extending from the proximal section 326A to the distal end 308A. The distal section 328A has an axial length that is approximately 50% of the axial length "L+X."

In the proximal section 326A of the tapered outer surface 322A, the outer geometry of the broach 302A defined by the stepped planes 314A is the same as the corresponding outer geometry of the sleeve 224A defined by the stepped walls 274A. In other words, the number of stepped planes 314A is equal to the number of stepped walls 274A, and each stepped plane 314A has the same maximum medial-lateral dimension, the same maximum anterior-posterior dimension, and the same axial height as the corresponding stepped wall 274A. For example, as shown in FIG. 24, the stepped planes 314A in the proximal section 326A define the same maximum medial-lateral dimension 290 and the same maximum anterior-posterior dimension 292 as the corresponding stepped wall 274A of the sleeve 224A. As a result, the broach 302A is configured to define a cavity in the patient's femur that includes a proximal section that is substantially the same as the sleeve 224A such that the sleeve 224A is fitted into that section.

In the distal section 328A of the tapered outer surface 322A the number of stepped planes 314A is equal to the number of stepped walls 274A, and each stepped plane 314A has the same axial height as the corresponding stepped wall 274A. However, the maximum medial-lateral dimension and the maximum anterior-posterior dimension of each stepped plane 314A are smaller than the maximum medial-lateral dimension and the maximum anterior-posterior dimension of the corresponding stepped wall 274A. In other words, the outer geometry of the broach 302A defined by the stepped planes 314A is smaller than the corresponding outer geometry of the sleeve 224A defined by the stepped walls 274A.

For example, as shown in FIG. 25, a stepped plane 314A in the distal section 328A defines a maximum medial-lateral dimension 330 that is less than the maximum medial-lateral dimension 294 of the corresponding stepped wall 274A. Similarly, the same stepped plane 314A in the distal section 328A defines a maximum anterior-posterior dimension 332 that is less than the maximum anterior-posterior dimension 296 of the corresponding stepped wall 274A. As a result, the broach 302A is configured to define a cavity in the patient's femur that includes a distal section that is smaller than the sleeve 224A such that the sleeve 224A is press fit into that section.

In the illustrative embodiment, the maximum medial-lateral dimension of each stepped plane 314A in the distal section 328A is 0.35 mm less than the maximum medial-lateral dimension of the corresponding stepped wall 274A of the sleeve 224A. Similarly, the maximum anterior-posterior dimension of each stepped plane 314A in the distal section 328A is 0.35 mm less than the maximum anterior-posterior dimension of the corresponding stepped wall 274A of the sleeve 224A. It should be appreciated that in other embodiments the dimensions of the broach 302A may be adjusted to provide greater or less press fit for the sleeve 224A. It should also be appreciated that the medial-lateral press fit and the anterior-posterior press fit may or may not be equal.

Furthermore, since the geometries of the outer surfaces 282A, 282B of the femoral metaphyseal sleeves 224A, 224B are essentially identical through axial length "L+X," the sleeve 224B will fit within a cavity prepared by the broach 302A in a patient's femur and extend distally from the bone by the distance "X+Y." As such, if the sleeve 224B is inserted into a cavity prepared by the broach 302A, the portion of the sleeve 224B corresponding to the distal section 328A of the broach 302A will be press fit, while the portion of the sleeve 224B corresponding to the proximal section 326A of the broach 302A will be fitted into that portion of the cavity.

As shown in FIG. 23, the body 306B of the broach 302B has a longitudinal axis 320B and a tapered outer surface 322B defined by the tips 324B of the cutting teeth 312B. The tapered outer surface 322B has an axial length "L+X+Y" defined along the axis 320B. In that way, the body 306B has the same axial height as the sleeve 224B. Additionally, the stepped planes 314B of the body 306B combine to define the axial length "L+X+Y" of the body 306B. In the illustrative embodiment, the number of stepped planes 314B is equal to the number of stepped walls 274B of the sleeve 224B; as such, each stepped plane 314B corresponds to a stepped wall 274B of the sleeve 224B.

The tapered outer surface 322B of the broach 302B has a proximal section 326B extending from the proximal tip 304B and a section 328B extending from the proximal section 326B to the distal end 308B. The distal section 328B has an axial length that is approximately 50% of the axial length "L+X+Y."

In the proximal section 326B of the tapered outer surface 322B, the outer geometry of the broach 302B defined by the stepped planes 314B is the same as the corresponding outer geometry of the sleeve 224B defined by the stepped walls 274B. In other words, the number of stepped planes 314B is equal to the number of stepped walls 274B, and each stepped plane 314B has the same maximum medial-lateral dimension, the same maximum anterior-posterior dimension, and the same axial height as the corresponding stepped wall 274B. As a result, the broach 302B is configured to define a cavity in the patient's femur that includes a proximal section that is substantially the same as the sleeve 224B such that the sleeve 224B is fitted into that section.

In the distal section 328B of the tapered outer surface 322B the number of stepped planes 314B is equal to the number of stepped walls 274B, and each stepped plane 314B has the same axial height as the corresponding stepped wall 274B. However, the maximum medial-lateral dimension and the maximum anterior-posterior dimension of each stepped plane 314B are smaller than the maximum medial-lateral dimension and the maximum anterior-posterior dimension of the corresponding stepped wall 274B. In other words, the outer geometry of the broach 302B defined by the stepped planes 314B is smaller than the corresponding outer geometry of the sleeve 224B defined by the stepped walls 274B. As a result, the broach 302B is configured to define a cavity in the patient's femur that includes a distal section that is smaller than the sleeve 224B such that the sleeve 224B is press fit into that section.

In the illustrative embodiment, the maximum medial-lateral dimension of each stepped plane 314B in the distal section 328B is 0.35 mm less than the maximum medial-lateral dimension of the corresponding stepped wall 274B of the sleeve 224B. Similarly, the maximum anterior-posterior dimension of each stepped plane 314B in the distal section 328B is 0.35 mm less than the maximum anterior-posterior dimension of the corresponding stepped wall 274B of the sleeve 224B. It should be appreciated that in other embodiments the dimensions of the broach 302B may be adjusted to provide greater or less press fit for the sleeve 224B.

Referring now to FIGS. 26-35, a plurality of augments 340 of the femoral components 200 are shown. The augments 340 include a plurality of distal augments 342, 344 (see FIGS. 26-29) and a plurality of posterior augments 346, 348. As described above, each of the augments 340 includes a mounting plug 256 that is configured to be received in the mounting aperture 250. Each augment 340 also includes a retention mechanism 350 configured secure the corresponding augment 340 to the femoral component 210, as described in greater detail below. In the illustrative embodiment, the augments 340 are formed from any suitable implant-grade metallic material such as, for example, cobalt-chromium, titanium, or stainless steel.

Figure 26:
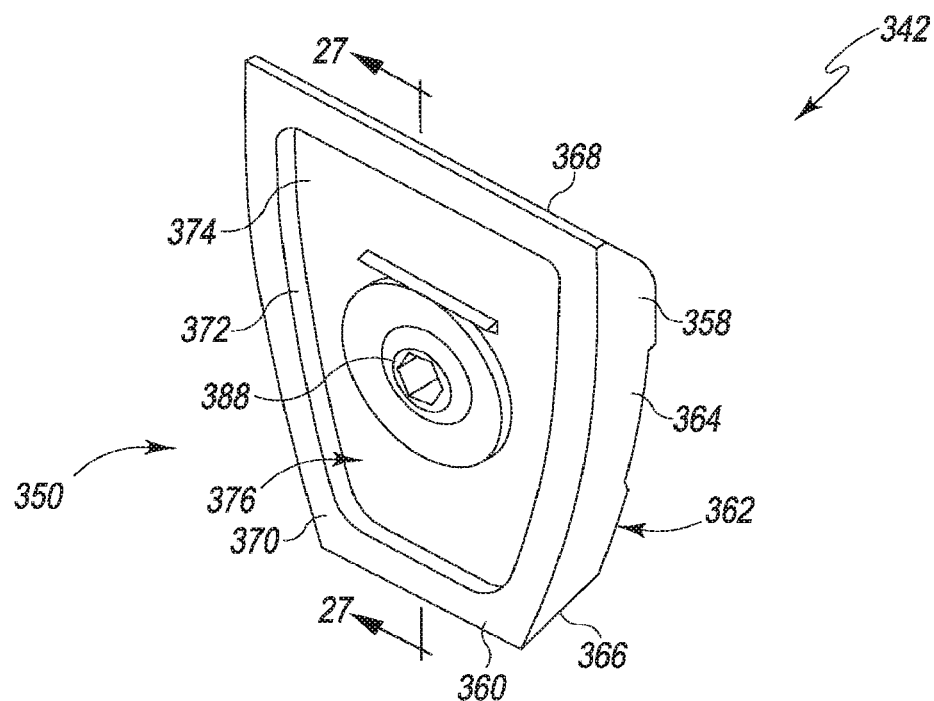
FIG. 26 is a perspective view of a distal augment for use with a femoral component of the modular knee prosthesis system of FIG. 15.
Figure 27:
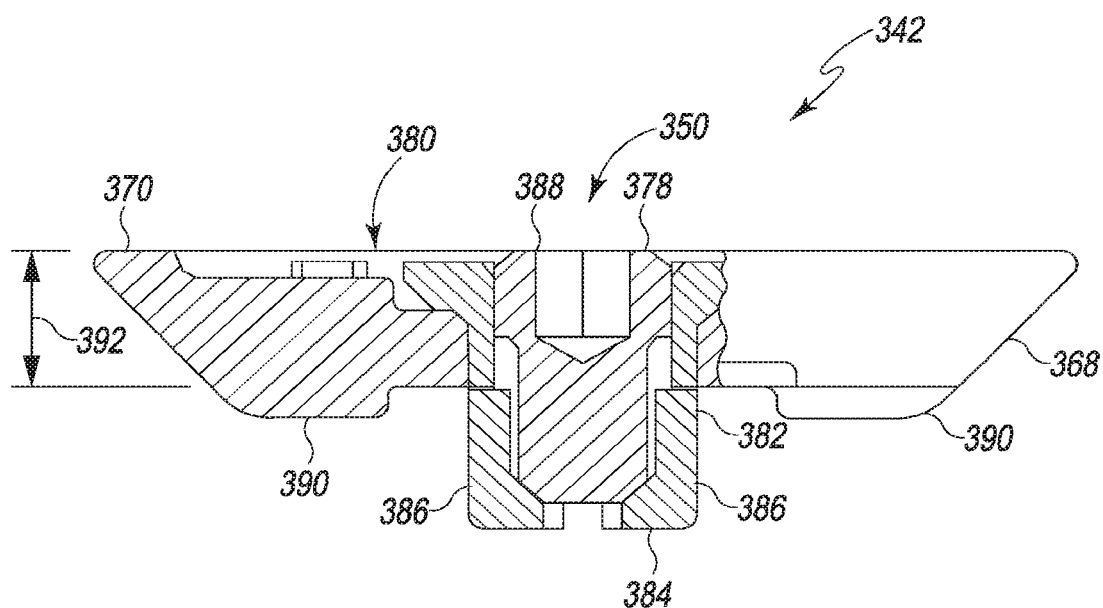
FIG. 27 is a fragmentary cross sectional view of the distal augment taken along the lines 27-27 in FIG. 26.

As shown in FIGS. 26-27, the distal augment 342 includes a wedge-shaped body 358 that has a proximal surface 360, a distal surface 362 positioned opposite the proximal surface 360, and a side wall 364 that connects the surfaces 360, 362. The side wall 364 includes a tapered anterior surface 366 and a tapered posterior surface 368, which extend obliquely relative the surfaces 360, 362. When the distal augment 342 is secured to the femoral component 210, the tapered anterior surface 366 is configured to engage the anterior chamfer surface 236 of the femoral component 210, and the tapered posterior surface 368 is configured to engage the posterior chamfer surface 234 of the femoral component 210.

As shown in FIG. 26, the proximal surface 360 of the distal augment 342 has a rim surface 370 and a side wall 372 that extends inwardly from the rim surface 370. The side wall 372 cooperates with a bottom surface 374 to define a pocket 376 in the proximal surface 360. The upper end 378 of the mounting plug 256 is positioned an opening 380 defined in the bottom surface 374, and the body 382 of the plug 256 extends through the augment body 358 to an end 384 positioned below the body 358, as shown in FIG. 27. The end 384 of the body 382 is divided into four legs 386.

The retention mechanism 350 of the augment 340 includes a fastener 388 that is threaded into the body 382 of the mounting plug 256. The fastener 288 includes a socket in which a driver may be inserted to rotate the fastener 288. When the fastener 388 is rotated in a first direction, the fastener 388 is driven toward the end 384 of the body 382, causing the legs 386 to expand outward; when the fastener is rotated in the opposite direction, the fastener 388 moves away from the end 384 of the body 382 such that the legs 386 are permitted to retract.

The distal surface 362 of the wedge-shaped body 358 is configured to engage the distal surface 230 of the femoral component 210. In the illustrative embodiment, a plurality of feet 390 extend from the distal surface 362 of the wedge-shaped body 358. Each foot 390 is sized to be positioned in the cement pocket 240 of the femoral component 210. As shown in FIG. 27, the wedge-shaped body 358 also has a thickness 392 defined between the distal surface 362 and the proximal surface 360.

Figure 28:
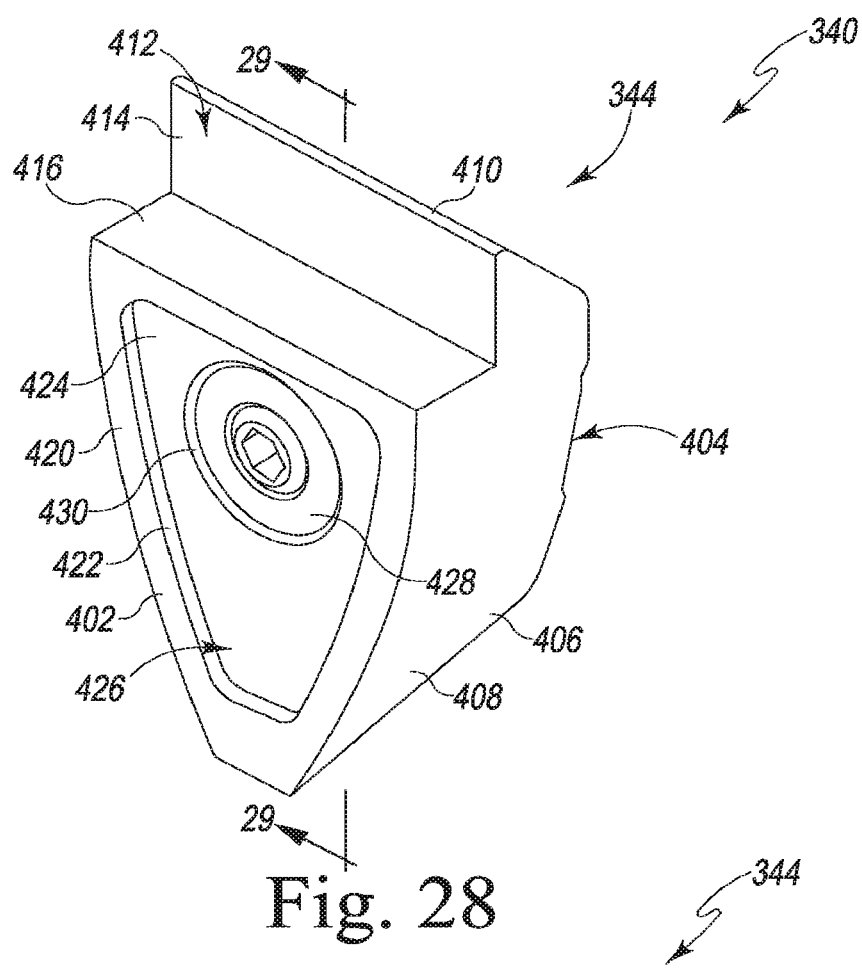
FIG. 28 is a perspective view of another size of distal augment for use with the femoral component of FIG. 15.
Figure 29:
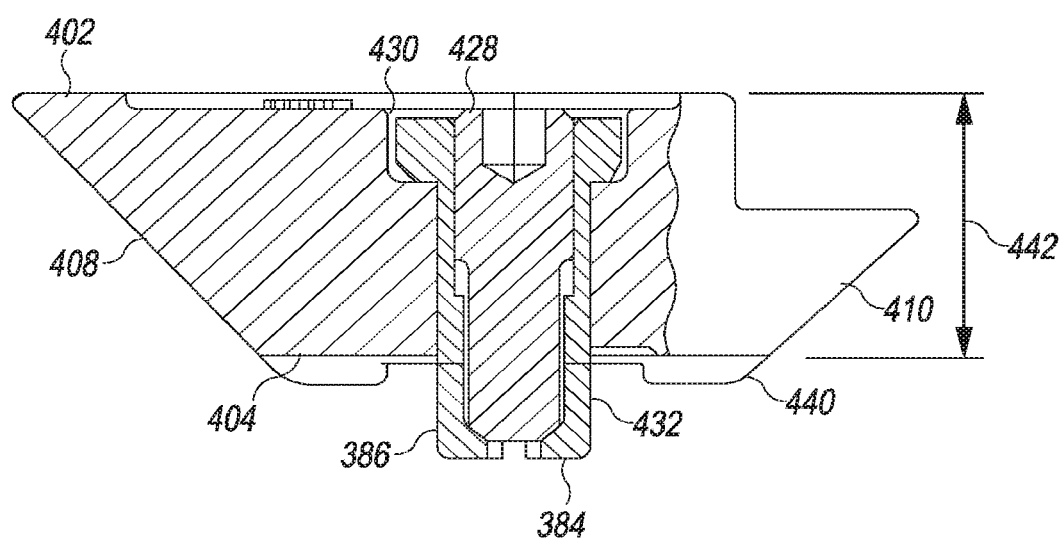
FIG. 29 is a fragmentary cross sectional view of the distal augment taken along the lines 29-29 in FIG. 28.

As shown in FIGS. 28-29, the distal augment 344 includes a wedge-shaped body 400 that has a proximal surface 402, a distal surface 404 positioned opposite the proximal surface 402, and a side wall 406 that connects the surfaces 402, 404. The side wall 406 includes a tapered anterior surface 408 and a tapered posterior surface 410, which extend obliquely relative to the surfaces 408, 410. When the distal augment 344 is secured to the femoral component 210, the tapered anterior surface 408 is configured to engage the anterior chamfer surface 236 of the femoral component 210, and the tapered posterior surface 410 is configured to engage the posterior chamfer surface 234 of the femoral component 210.

The side wall 406 has a posterior notch 412 defined therein. As shown in FIGS. 28-29, the notch 412 is defined by a substantially planar proximal surface 414 extending parallel to the proximal surface 402 and anteriorly from an edge of the tapered posterior surface 410 and a substantially planar posterior surface 416 extending orthogonal to the proximal surface 414. The notch 412 is sized to receive the posterior augment 348, as described in greater detail below.

As shown in FIG. 28, the proximal surface 402 of the distal augment 344 has a configuration similar to the proximal surface 360 of the distal augment 342. The surface 402 has a rim surface 420 and a side wall 422 that extends inwardly from the rim surface 420. The side wall 422 cooperates with a bottom surface 424 to define a pocket 426 in the proximal surface 402. The upper end 428 of the mounting plug 256 is positioned an opening 430 defined in the bottom surface 424, and the body 432 of the plug 256 extends through the augment body 358 to an end 384 positioned below the body 358, as shown in FIG. 29. The end 384 of the body 432 is divided into four legs 386.

The retention mechanism 350 of the augment 340 includes a fastener 438 that is threaded into the body 432 of the mounting plug 256. The fastener 438 includes a socket in which a driver may be inserted to rotate the fastener 438. When the fastener 438 is rotated in a first direction, the fastener 438 is driven toward the end 384 of the body 432, causing the legs 386 to expand outward; when the fastener is rotated in the opposite direction, the fastener 438 moves away from the end 384 of the body 432 such that the legs 386 are permitted to retract.

The distal surface 404 of the wedge-shaped body 400 is configured to engage the distal surface 230 of the femoral component 210. In the illustrative embodiment, a plurality of feet 440 extend from the distal surface 404 of the wedge-shaped body 400. Each foot 440 is sized to be positioned in the cement pocket 240 of the femoral component 210. As shown in FIG. 29, the wedge-shaped body 358 also has a thickness 442 defined between the distal surface 404 and the proximal surface 402.

As shown in FIGS. 27 and 29, the thickness 442 of the augment 344 is greater than the thickness 392 of the augment 342. In the illustrative embodiment, the thickness 392 is equal to approximately 4 millimeters, and the thickness 442 is equal to approximately 12 millimeters. It should be appreciated that in other embodiments the thicknesses of the augments may increase or decrease depending with the size of the other femoral components 200. Additionally, as shown in FIGS. 27 and 29, the distal surface 404 of the augment 344 is wider than distal surface 362 of the augment 342.

As described above, the femoral components 200 also include posterior augments 346, 348. Each of the posterior augments 346, 348 includes a body 450 having an anterior surface 452 and a posterior surface 454 positioned opposite the anterior surface 452. As shown in FIGS. 30 and 32, each of the posterior augments 346, 348 includes the mounting plug 256, which has a configuration similar to the configurations described above in regard to the distal augments 342, 344.

The posterior surface 454 of the body 450 is configured to engage the posterior fixation surface 232 of the femoral component 210. In the illustrative embodiment, a plurality of feet 456 extend from the posterior surface 454. Each foot 456 is sized to be positioned in the cement pocket 240 of the femoral component 210. As shown in FIG. 30, the posterior augment 346 has a thickness 460 defined between the anterior surface 452 and the posterior surface 454; as shown in FIG. 32, the posterior augment 348 has a thickness 462 defined between the anterior surface 452 and the posterior surface 454. In the illustrative embodiment, the thickness 462 of the augment 348 is greater than the thickness 460 of the augment 346.

In use, the augments 340 may be attached to the femoral component 210 in the same sequence, regardless of the combination of augments 340 used. For example, as shown in FIGS. 30-31, the posterior augment 346 may be attached first to the posterior fixation surface 232 of the femoral component 210 via the mounting plug 256, which is inserted into the aperture 260. Using the fastener (not shown) of the mounting plug 256, the legs 386 of the mounting plug 256 are expanded into engagement with the wall 252 defining the aperture 250, thereby securing the augment 346 to the posterior fixation surface 232.

The distal augment 342 may then be attached to the distal fixation surface 230. As shown in FIG. 31, the mounting plug 256 is aligned with the aperture 250 of the distal fixation surface 230. The distal augment 342 may be advanced downward such that the plug 256 is received in the aperture 250. The fastener 388 may then be operated to engage the wall 252 with the legs 386 of the mounting plug 256, thereby securing the augment 342 to the distal fixation surface 230.

As shown in FIGS. 32-35, another combination of augments 340—in this case, the largest augments 344, 348—may attached in the same sequence as the augments 342, 346. To do so, the posterior augment 348 may be attached first to the posterior fixation surface 232 of the femoral component 210 via the mounting plug 256, which is inserted into the aperture 260. Using the fastener (not shown) of the mounting plug 256, the legs 386 of the mounting plug 256 are expanded into engagement with the wall 252 defining the aperture 250, thereby securing the augment 348 to the posterior fixation surface 232.

The distal augment 344 may then be attached to the distal fixation surface 230. To do so, the distal augment 344 is positioned above the distal fixation surface 230 as shown in FIG. 33. The augment 344 may then be rotated as shown in FIG. 34 and advanced downward.

Figure 34:
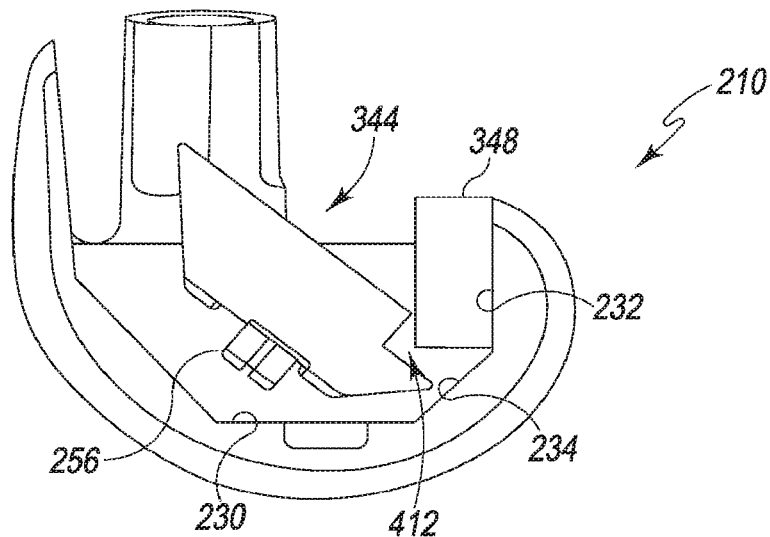
FIG. 34 is a view similar to FIGS. 32-33 showing the installation of the distal augment of FIGS. 28-29.
Figure 35:
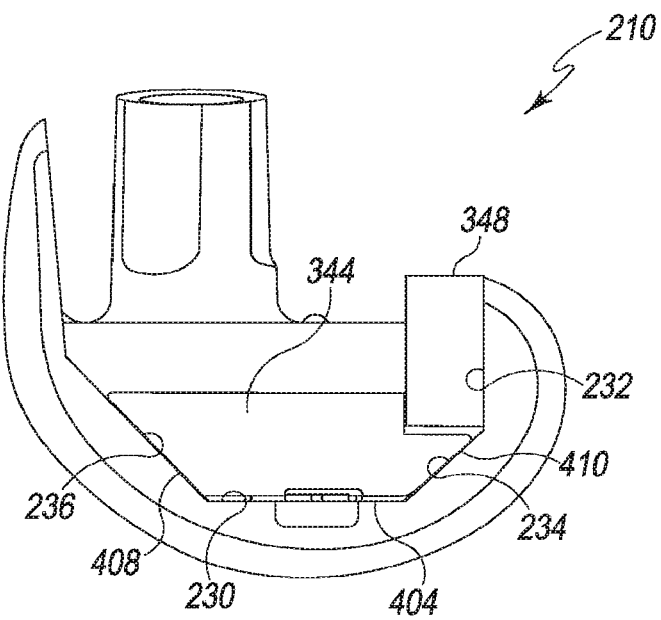
FIG. 35 is a view similar to FIGS. 32-34 showing the posterior augment and the distal augment secured to the femoral component.

As shown in FIG. 34, the user may slide posterior edge of the distal augment 344 under the posterior augment 348 to "hook" the distal augment 344 into position. In doing so, the posterior augment 348 is advanced into the posterior notch 412 of the distal augment 344. When the plug 256 of the distal augment 344 is received in the aperture 250 and the augment 344 is properly seated as shown in FIG. 35, the posterior augment 348 remains in the posterior notch 412. The fastener 388 may then be operated to engage the wall 252 with the legs 386 of the mounting plug 256, thereby securing the augment 348 to the distal fixation surface 230.

Figure 36:
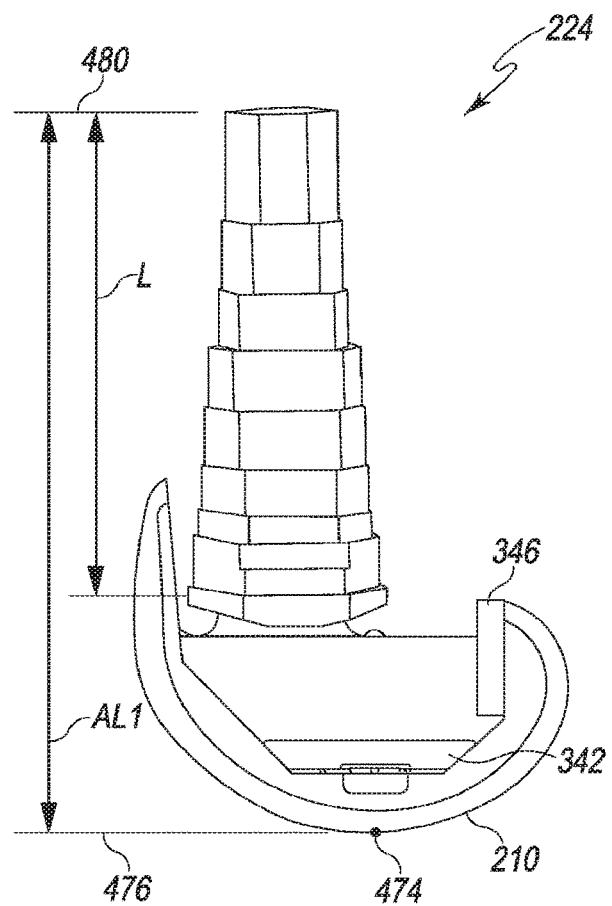
FIG. 36 is an anterior-posterior view of a modular knee prosthesis system of FIG. 15 using the metaphyseal sleeve of FIG. 16 and the augments of FIGS. 30-31.
Figure 37:
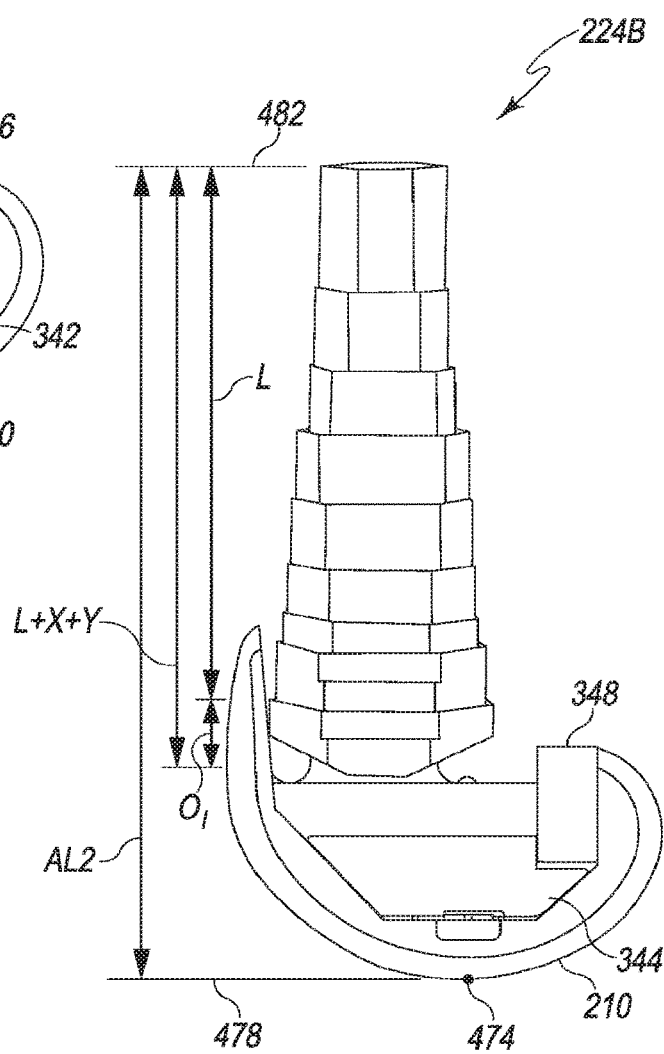
FIG. 37 is an anterior-posterior view similar to FIG. 36 showing the metaphyseal sleeve of FIG. 18 and the augments of FIGS. 32-35.

As shown in FIGS. 36-37, the femoral components 200 may be assembled to form a femoral orthopaedic prosthesis. In FIG. 36, the smallest femoral sleeve 224 and the smallest augments 342, 346 are assembled with the femoral component 210 to form prosthesis 470. In FIG. 37, the largest femoral sleeve 224B and the largest augments 344, 348 are assembled with the femoral component 210 to form prosthesis 472. As shown in FIGS. 36-37, the distal-most points 474 of the condyle surfaces 12, 14 define a joint line of the femoral orthopaedic prosthesis when the patient's leg is in extension. In FIG. 36, the joint line is indicated by line 476; in FIG. 37, the joint line is indicated by line 478.

The illustrated assemblies have maximum axial lengths from planes at the proximal ends 266, 266B (the planes shown at 480 and 482) to the plane of the joint line, shown at 476 in FIG. 36 and at 478 in FIG. 37. These maximum axial lengths of the assemblies are shown at AL1 in FIG. 36 and AL2 in FIG. 37. In the illustrative embodiment, AL2 is longer than AL1 by the dimension "X+Y", that is the axial length of the sleeve 224B beyond the length "L" of the smallest sleeve 224.

As can also be seen from a comparison of FIGS. 36-37, using the larger sleeve 224B distalizes the joint line 476 to the position 478 by the offset distance $o_1$. This offset distance $o_1$ also corresponds with the dimension "X+Y". Similarly, using the sleeve 224A distalizes the joint line by the dimension "X" relative to the joint line 476.

Since the geometries of the stepped bodies 264, 264B, 264C of the different sizes of sleeves 224, 224A, 224B are the same through axial length "L", the surgeon can prepare the distal femur using the broach 302 to receive the smallest size of femoral sleeve 224. If the surgeon determines intraoperatively that the joint line should be distalized, the surgeon may use any of the other sizes of sleeve 224A, 224B, and the proximal portion of the larger size sleeve will fit within the opening prepared in the femur to receive the smaller sleeve and extend distally from the bone by the distance "X" or "X+Y" o thereby distally offset the joint line. In the illustrative embodiment, the thickness 442 of the distal augment 344 is equal to the offset distance $o_1$ such that the sleeve 224B the prosthesis 472 may be stabilized when the joint line is distalized. The surgeon can therefore accomplish this distalization without any further preparation of the bone cavity.

Another system providing the option of distalizing the joint line is disclosed in the application for United States patent filed concurrently herewith entitled "Knee Prosthesis System with Standard and Distally Offset Joint Line," (Ser. No. 61/703,412), filed by Peter J. James, Richard E. Jones, Benjamin J. Sordelet, Timothy G. Vendrely and Stephanie M. Wainscott, which is incorporated by reference herein in its entirety.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic knee system, comprising:
    a prosthetic knee component configured to be implanted into an end of a long bone that forms a knee joint of a patient, the prosthetic knee component including a stem,
    a first monolithic sleeve component configured to be secured to the stem of the prosthetic knee component, the first monolithic sleeve component including a first plurality of steps that define an axial length L, each step of the first plurality of steps having a maximum medial-lateral dimension, a maximum anterior-posterior dimension, and an axial step height, and
    a second monolithic sleeve component configured to be secured to the stem of the prosthetic knee component in place of the first monolithic sleeve component, the second monolithic sleeve component including a second plurality of steps that define an axial length L+X, each step of the second plurality of steps having a maximum medial-lateral dimension, a maximum anterior-posterior dimension, and an axial step height,
    wherein the first monolithic sleeve component has an outer three-dimensional geometry over the axial length L that is identical to an outer three-dimensional geometry over the axial length L of the second monolithic sleeve component such that the maximum medial-lateral dimensions, the maximum anterior-posterior dimensions, and the axial step heights of the first plurality of steps over the axial length L of the first monolithic sleeve component are equal to the corresponding maximum medial-lateral dimensions, maximum anterior-posterior dimensions, and axial step heights of the second plurality of steps over the axial length L of the second monolithic sleeve component, and
    wherein at least one of the maximum medial-lateral dimension and the maximum anterior-posterior dimension of any step of the second plurality of steps over the axial length X of the second monolithic sleeve component is greater than the maximum medial-lateral dimension, the maximum anterior-posterior dimension, and the axial step height of any step of the second plurality of steps over the axial length L of the second monolithic sleeve component.

2. The orthopaedic knee system of claim 1, wherein:
    the first monolithic sleeve component includes a first tip, a first base configured to be secured to the stem of the prosthetic knee component, and a first body including the first plurality of steps and extending the axial length L between the first tip and the first base, and the second monolithic sleeve component includes a second tip, an upper body section including a portion of the second plurality of steps and extending the axial length L from the second tip, a lower body section including a portion of the second plurality of steps and extending the axial length X from the upper body section to a second base configured to be secured to the stem of the prosthetic knee component in place of the first monolithic sleeve component.

3. The orthopaedic knee system of claim 2, wherein the first monolithic component has an outer surface that tapers between the first tip and the first base.

4. The orthopaedic knee system of claim 3, wherein the second monolithic component has an outer surface that tapers between the second tip and the second base.

5. The orthopaedic knee system of claim 2, further comprising an augment component configured to be coupled to the prosthetic knee component.

6. The orthopaedic knee system of claim 1, further comprising a first broach including (i) a first end configured to be separately secured to a handle and (ii) a first tapered body extending distally from a second end positioned opposite the first end, the first tapered body having a plurality of cutting teeth configured to define a cavity sized to receive the portion of the first monolithic sleeve component extending the axial length L.

7. The orthopaedic knee system of claim 6, further comprising a second broach including (i) a first end configured to be separately secured to the handle in place of the first broach, (ii) a first tapered body extending distally from a second end positioned opposite the first end, the first tapered body having a plurality of cutting teeth extending an axial length L, and (iii) a second tapered body extending distally from the first tapered body, the second tapered body having a plurality of cutting teeth extending an axial length X,
wherein the first tapered body of the first broach and the first tapered body of the second broach have matching outer dimensional geometries and the second tapered body has a second outer dimensional geometry different from the first outer dimensional geometries.

8. An orthopaedic knee system, comprising:
a femoral component configured to be implanted into an end of a patient's femur, the femoral component including a stem,
a first metaphyseal member configured to be secured to the stem of the femoral component, the first metaphyseal member including a first plurality of steps that define an axial length L, each step of the first plurality of steps having a maximum medial-lateral dimension, a maximum anterior-posterior dimension, and an axial step height, and
a second metaphyseal member configured to be secured to the stem of the femoral component in place of the first metaphyseal member, the second metaphyseal member including a second plurality of steps that define an axial length L+X, each step of the second plurality of steps having a maximum medial-lateral dimension, a maximum anterior-posterior dimension, and an axial step height,
wherein the first metaphyseal member has an outer three-dimensional geometry over the axial length L that is identical to an outer three-dimensional geometry over the axial length L of the second metaphyseal member such that the maximum medial-lateral dimensions, the maximum anterior-posterior dimensions, and the axial step heights of the first plurality of steps over the axial length L of the first metaphyseal member are equal to the corresponding maximum medial-lateral dimensions, maximum anterior-posterior dimensions, and axial step heights of the second plurality of steps over the axial length L of the second metaphyseal member, and
wherein at least one of the maximum medial-lateral dimension and the maximum anterior-posterior dimension of any step of the second plurality of steps over the axial length X of the second metaphyseal member is greater than the maximum medial-lateral dimension, the maximum anterior-posterior dimension, and the axial step height of any step of the second plurality of steps over the axial length L of the second metaphyseal member.

9. The orthopaedic knee system of claim 8, wherein:
the first metaphyseal member includes a first proximal tip, a first distal base configured to be secured to the stem of the femoral component, and a first body including the first plurality of steps and extending the axial length L between the first proximal tip and the first distal base, and
the second metaphyseal member includes a second proximal tip, a proximal body section including a portion of the second plurality of steps and extending the axial length L from the second proximal tip, a distal body section including a portion of the second plurality of steps and extending the axial length X from the proximal body section to a second distal base configured to be secured to the stem of the femoral component in place of the first metaphyseal member.

10. The orthopaedic knee system of claim 9, wherein the first metaphyseal member has an outer surface that tapers between the first proximal tip and the first distal base.

11. The orthopaedic knee system of claim 10, wherein the second metaphyseal member has an outer surface that tapers between the second proximal tip and the second distal base.

12. An orthopaedic knee system, comprising:
a tibial component configured to be implanted into an end of a patient's tibia, the tibial component including a stem,
a first metaphyseal member configured to be secured to the stem of the tibial component, the first metaphyseal member including a first plurality of steps that define an axial length L, each step of the first plurality of steps having a maximum medial-lateral dimension, a maximum anterior-posterior dimension, and an axial step height, and
a second metaphyseal member configured to be secured to the stem of the tibial component in place of the first metaphyseal member, the second metaphyseal member including a second plurality of steps that define an axial length L+X, each step of the second plurality of steps having a maximum medial-lateral dimension, a maximum anterior-posterior dimension, and an axial step height,
wherein the first metaphyseal member has an outer three-dimensional geometry over the axial length L that is identical to an outer three-dimensional geometry over the axial length L of the second metaphyseal member such that the maximum medial-lateral dimensions, the maximum anterior-posterior dimensions, and the axial step heights of the first plurality of steps over the axial length L of the first metaphyseal member are equal to the corresponding maximum medial-lateral dimensions, maximum anterior-posterior dimensions, and axial step heights of the second plurality of steps over the axial length L of the second metaphyseal member, and wherein at least one of the maximum medial-lateral dimension and the maximum anterior-posterior dimension of any step of the second plurality of steps over the axial length X of the second metaphyseal member is greater than the maximum medial-lateral dimension, the maximum anterior-posterior dimension, and the axial step height of any step of the second plurality of steps over the axial length L of the second metaphyseal member.

13. The orthopaedic knee system of claim 12, wherein:
the first metaphyseal member includes a first distal tip, a first proximal base configured to be secured to the stem of the tibial component, and a first body including the first plurality of steps and extending the axial length L between the first distal tip and the first proximal base, and the second metaphyseal member includes a second distal tip, an distal body section including a portion of the second plurality of steps and extending the axial length L from the second distal tip, an upper body section including a portion of the second plurality of steps and extending the axial length X from the distal body section to a second proximal base configured to be secured to the stem of the tibial component in place of the first metaphyseal member.

14. The orthopaedic knee system of claim 13, wherein the first metaphyseal member has an outer surface that tapers between the first distal tip and the first proximal base.

15. The orthopaedic knee system of claim 13, wherein the second metaphyseal member has an outer surface that tapers between the second distal tip and the second proximal base.

* * * * *